(12) United States Patent
Shaunak

(10) Patent No.: US 6,689,764 B1
(45) Date of Patent: Feb. 10, 2004

(54) TREATMENT OF ANGIOGENESIS DEPENDENT CONDITIONS WITH DEXTRIN SULPHATE

(75) Inventor: Sunil Shaunak, Hertfordshire (GB)

(73) Assignee: ML Laboratories PLC, London (GB)

(*) Notice: Subject to any disclaimer, the term of this patent is extended or adjusted under 35 U.S.C. 154(b) by 33 days.

(21) Appl. No.: 10/031,354

(22) PCT Filed: Jul. 24, 2000

(86) PCT No.: PCT/GB00/02799

§ 371 (c)(1),
(2), (4) Date: May 31, 2002

(87) PCT Pub. No.: WO01/07057

PCT Pub. Date: Feb. 1, 2001

(30) Foreign Application Priority Data

Jul. 22, 1999 (GB) .............................. 9917092

(51) Int. Cl.[7] ..................... A61K 31/737; A61K 31/715; A61P 13/12; A61P 19/02; A61P 27/02

(52) U.S. Cl. ............................ 514/58; 514/54; 514/60; 536/103; 536/123.1; 536/102

(58) Field of Search .............................. 514/58, 54, 60; 536/103

(56) References Cited

U.S. PATENT DOCUMENTS

4,900,815 A    2/1990   Tanaka et al. ................. 536/54

FOREIGN PATENT DOCUMENTS

| WO | WO 98/24421 | 6/1998 | .......... A61K/31/00 |
| WO | WO 99/06025 | 2/1999 | ............ A61K/9/12 |

OTHER PUBLICATIONS

Folkman et al, "Control of Angiogenesis with Synthetic Heparin Substitutes" *Science* 243, pp. 1490–1493 (1989).
De Clercq, Erik; "Anti–HIV Activity of Sulfated Polysaccharides" *Carbohydrates and Carbohydrate Polymers, Analysis, Biotechnology, Modification, Antiviral, Biomedical and Other Applications*, Chapter 9, pp. 87–100 (1993).
Franz et al.; "Pharmacological Activities of Sulfated Carbohydrate Polymers" *Bioactive Carbohydrate Polymers*, pp. 47–58 (2000).
Hahnenberger et al.; "Antiangiogenic Effect of Sulphated and Nonsulphated Glycosaminoglycans and Polysaccharides in the Chick Embryo Chorioallantoic Membrane" *Glycoconjugate Journal* 8, pp. 350–353 (1991).
Hirohata et al.; "Angioneogenesis as a Possible Elusive Triggering Factor in Rheumatoid Arthritis" *The Lancet* 353, p. 1331 (1999).
Watson et al.; "Inhibitory Effects of the Gastrin Receptor Antagonist CR2093 on Basal, Gastrin–Stimulated and Growth Factor–Stimulated Growth of the Rate Pancreatic Cell Line AR42J" *Anti–Cancer Drugs* 4. pp. 591–597 (1994).
Thornton et al.; "Anti–Kaposi's Sarcoma and Antiangiogenic Activities of Sulfated Dextrins" *Antimicrobial Agents and Chemotherapy* 43:10 pp. 2528–2533 (1999).
International Search Report for PCT/GB00/02799; mailed Nov. 22, 2000.

*Primary Examiner*—Samuel Barts
*Assistant Examiner*—Michael C. Henry
(74) *Attorney, Agent, or Firm*—Myers Bigel Sibley & Sajovec, PA

(57) ABSTRACT

The invention relates to the inhibitory effects of dextrin sulphate on angiogenesis and in particular the treatment of diseases or disorders which would benefit from the administration of dextrin sulphate.

27 Claims, 26 Drawing Sheets

Figure 3:
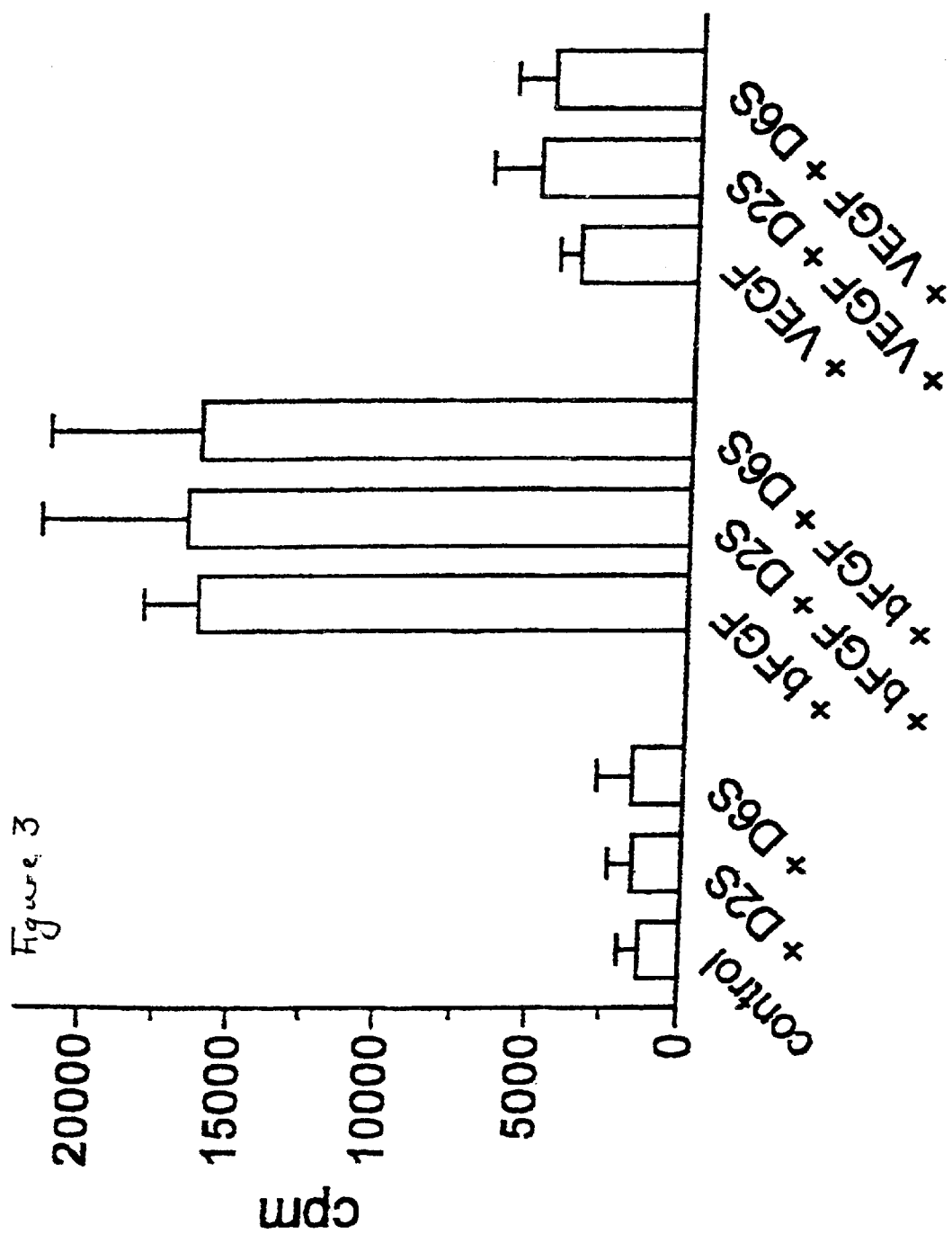

Figure 1    Internalisation of D2S and D6S by different cell types

| Cell type | Dextrin sulphate internalised |
|---|---|
| Peritoneal macrophages | Yes |
| Peritoneal macrophages from patients with AIDS | Yes |
| Peripheral blood mononuclear cells | No |
| Monocytes | No |
| Monocyte-derived-macrophages | No |
| HPB-ALL | No |
| H9 | No |
| Jurkat | No |
| U1 | No |
| U937 | No |
| U38 | No |
| HUVECs | No |
| HeLa | No |
| C11STH | No |
| KSY-1 | No |
| RBE4 | No |
| U87 | No |

Figure 2    Endothelial microtubule formation in the presence of sulphated dextrins

| Compound | | Tube formation score |
|---|---|---|
| Dextrin | | 4 |
| D2S | (μg/ml) | |
| | 0 | 4 |
| | 6.25 | 4 |
| | 12 | 4 |
| | 25 | 4 |
| | 50 | 3 |
| | 100 | 3 |
| | 200 | 2 |
| D6S | (μg/ml) | |
| | 0 | 4 |
| | 6.25 | 4 |
| | 12 | 3 |
| | 25 | 2 |
| | 50 | 1 |
| | 100 | 0 |
| | 200 | 0 |

Figure 11

| Cell line | Expt No | Cell conc | Inhibition at 1000 μg/ml (%) | p value |
|---|---|---|---|---|
| SK-HEP-1 | 1 | 1e4 | 64.3 | p<0.0001 |
| | | 2e4 | 39.0 (500μg/ml) | p<0.0001 |
| | 2 | 1e4 | 63.6 | p<0.0001 |
| | | 2e4 | 35.1 | p<0.0001 |
| ECV304 | 1 | 1e4 | 21.5 | p<0.0001 |
| | | 2e4 | 33.1 | p<0.0001 |
| | 2 | 1e4 | 11.9 | p<0.01 |
| | | 2e4 | 12.8 | p<0.0001 |

Figure 12  Mean (SD) angiogenesis measurements

| Tubule no. | Distance between tubules | No. tubule branch points | Tubule no. | Distance between tubules | No. tubule branch points |
|---|---|---|---|---|---|
| Suramin (n=80) <br> 40.5 (23.24) <br> p<0.001 | 40.51 (20.30) | 0.05 (0.23) <br> p<0.0001 | 10µg Dextrin sulphate (n=151) <br> 76 (43.73) <br> NS | 86.31 (56.90) | 1.62 (3.36) <br> p<0.01 |
| VEGF (n=286) <br> 143.5 (82.71) <br> p<0.0001 | 85.53 (53.41) | 4.00 (5.64) <br> p<0.05 | 50µg Dextrin sulphate (n=121) <br> 61 (35.07) <br> p<0.0001 | 87.04 (58.57) | 0.85 (1.95) <br> p<0.0001 |
| 0µg Dextrin sulphate (n=164) <br> 82.5 (47.49) | 89.25 (65.40) | 3.05 (4.43) | 100µg Dextrin sulphate (n=85) <br> 43 (24.68) <br> p<0.0001 | 94.73 (63.51) | 0.89 (1.43) <br> p<0.0001 |
| 1µg Dextrin sulphate (n=197) <br> 99 (57.01) <br> p<0.0001 | 80.33 (56.36) | 2.12 (3.76) <br> p<0.05 | 500µg Dextrin sulphate (n=77) <br> 39 (22.37) <br> p<0.0001 | 77.30 (44.27) | 0.33 (0.66) <br> p<0.0001 |
| 5µg Dextrin sulphate (n=189) <br> 95 (54.70) <br> p<0.05 | 72.38 (50.42) | 1.39 (2.78) <br> p<0.0001 | 1000µg Dextrin sulphate (n=52) <br> 26.5 (15.16) <br> p<0.0001 | 69.47 (35.74) | 0.24 (0.53) <br> p<0.0001 |

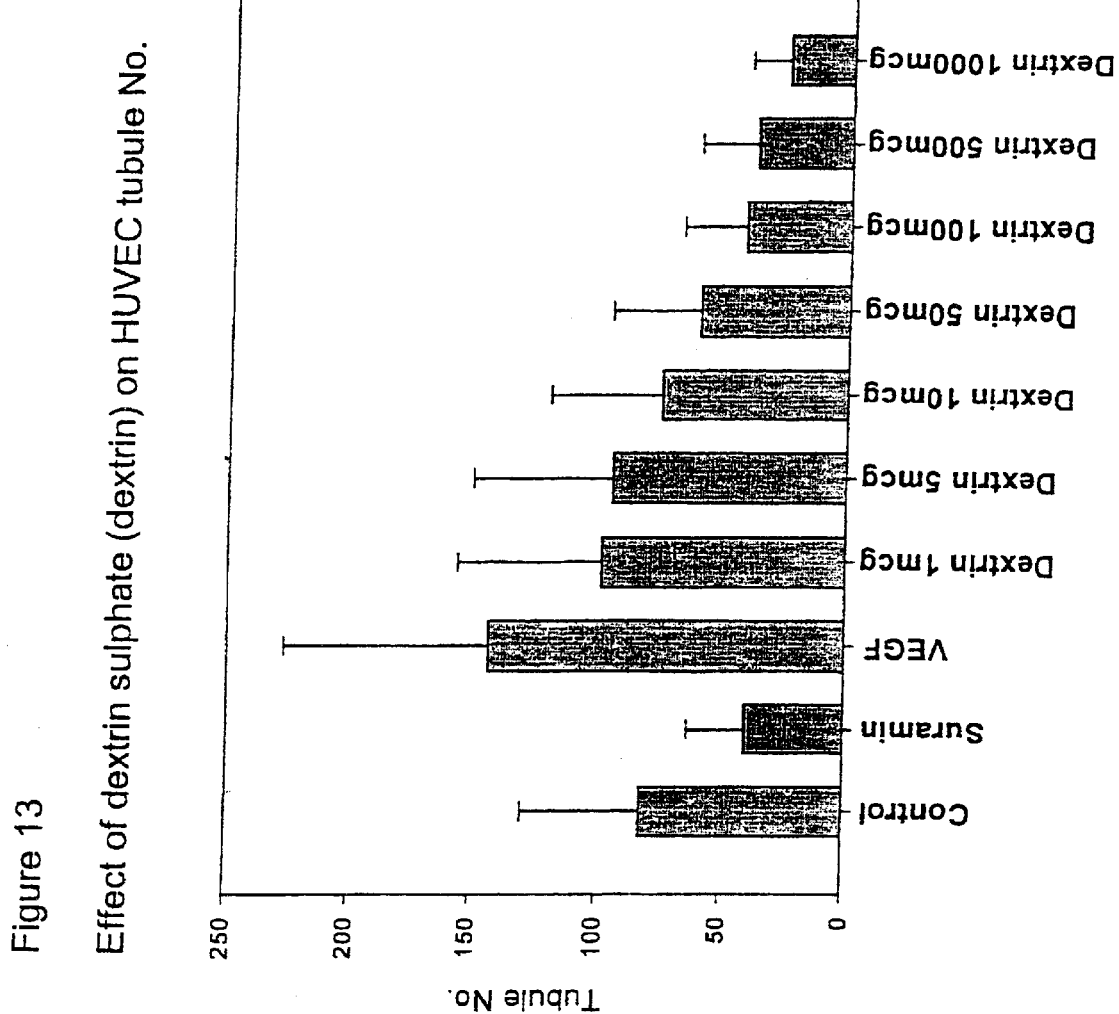
Figure 13 Effect of dextrin sulphate (dextrin) on HUVEC tubule No.

Effect of dextrin sulphate (dextrin) on the branch points of HUVEC tubules

Figure 15a: Suramin

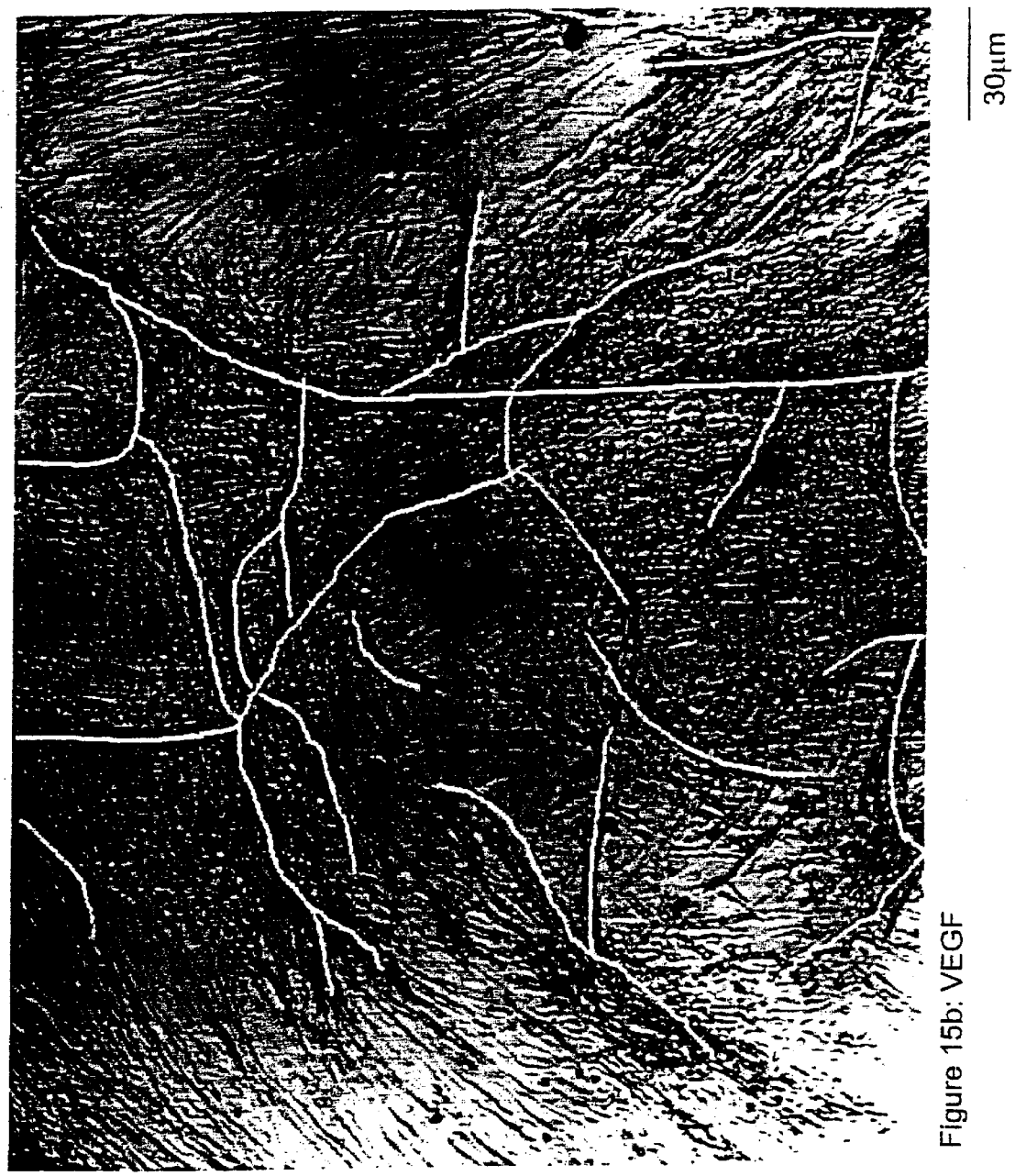
Figure 15b: VEGF

Figure 16a: 0µg dextrin sulphate

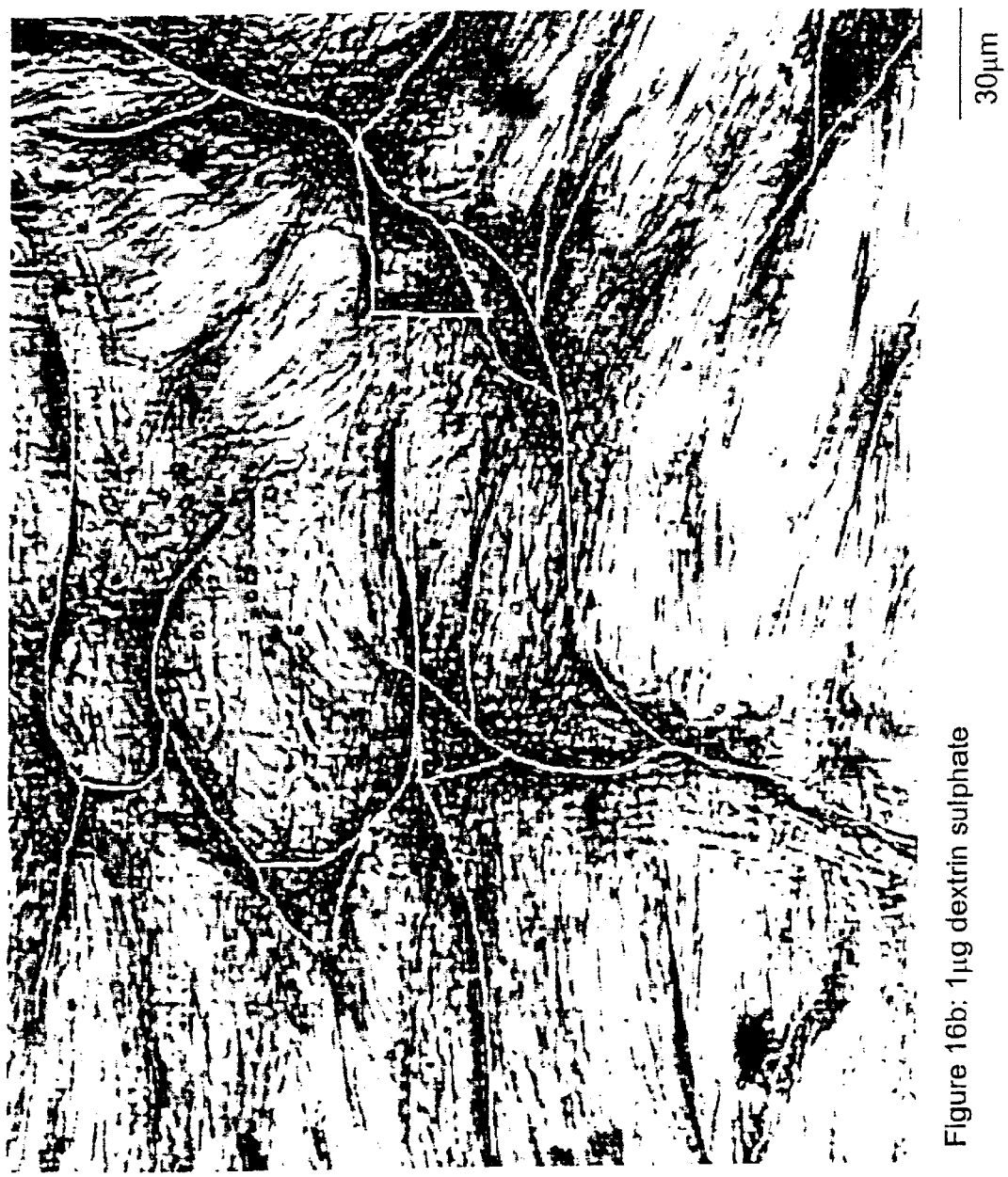
Figure 16b: 1μg dextrin sulphate

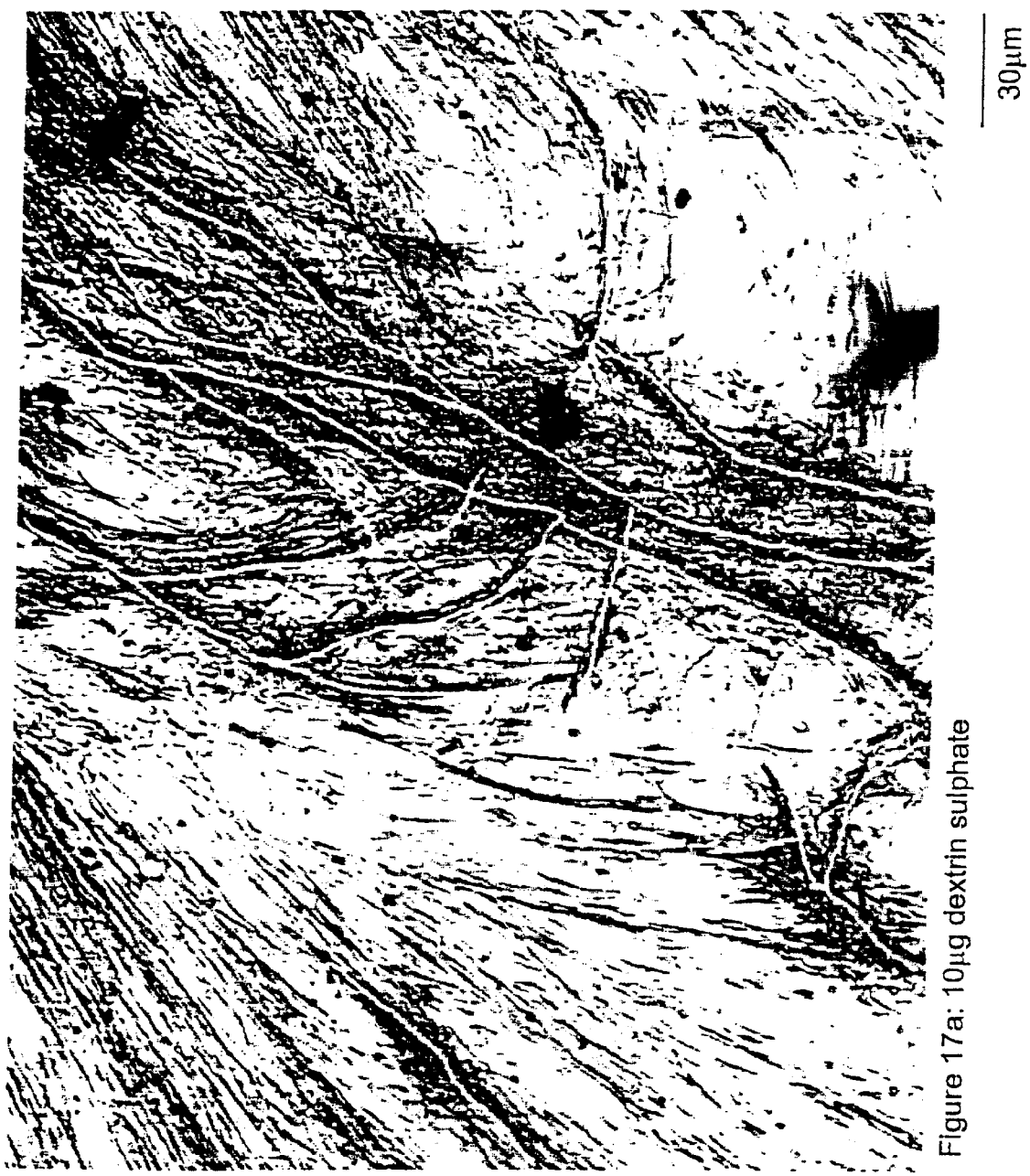
Figure 17a: 10μg dextrin sulphate

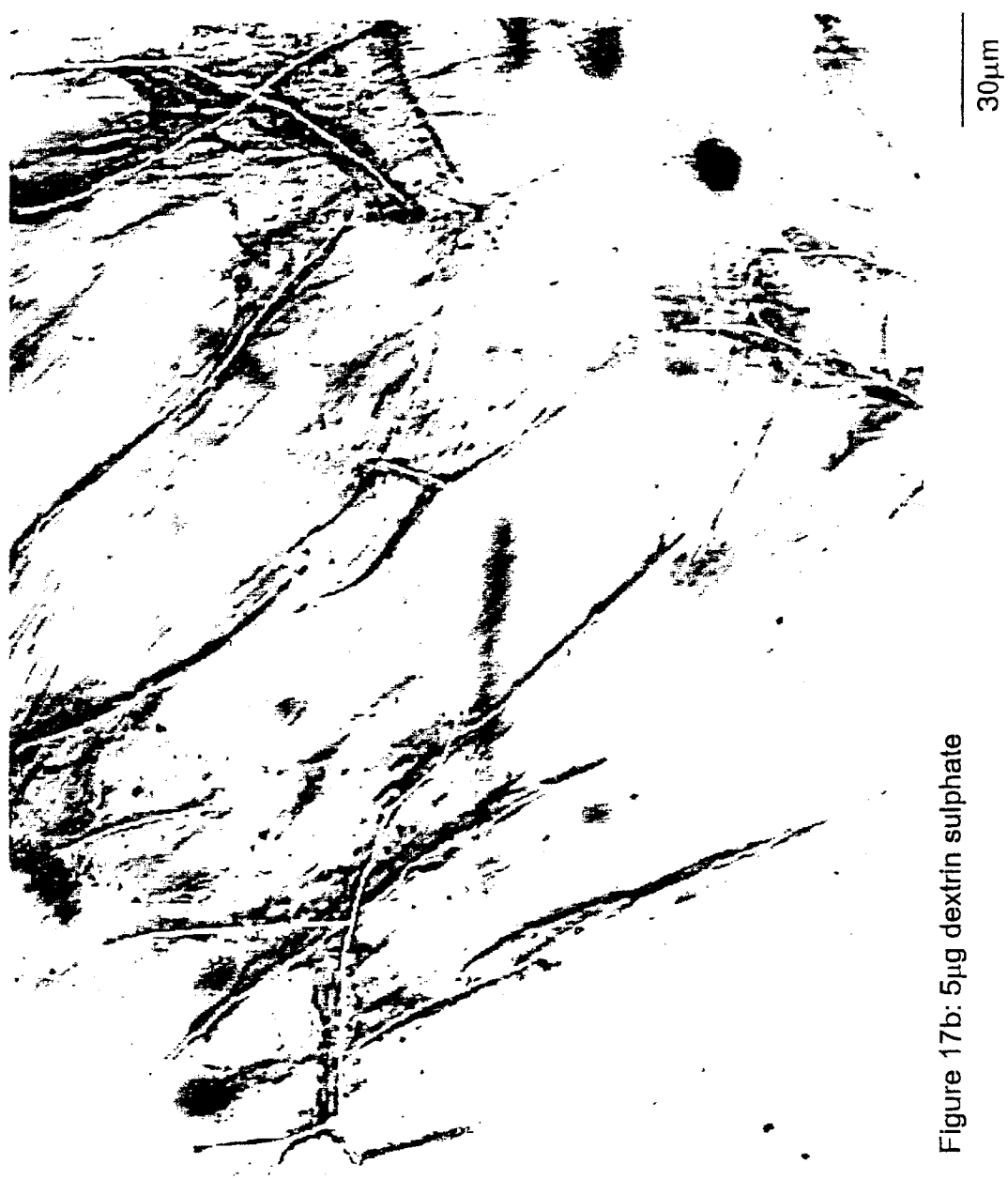
Figure 17b: 5μg dextrin sulphate

Figure 18a: 50μg dextrin sulphate

Figure 18b: 100μg dextrin sulphate

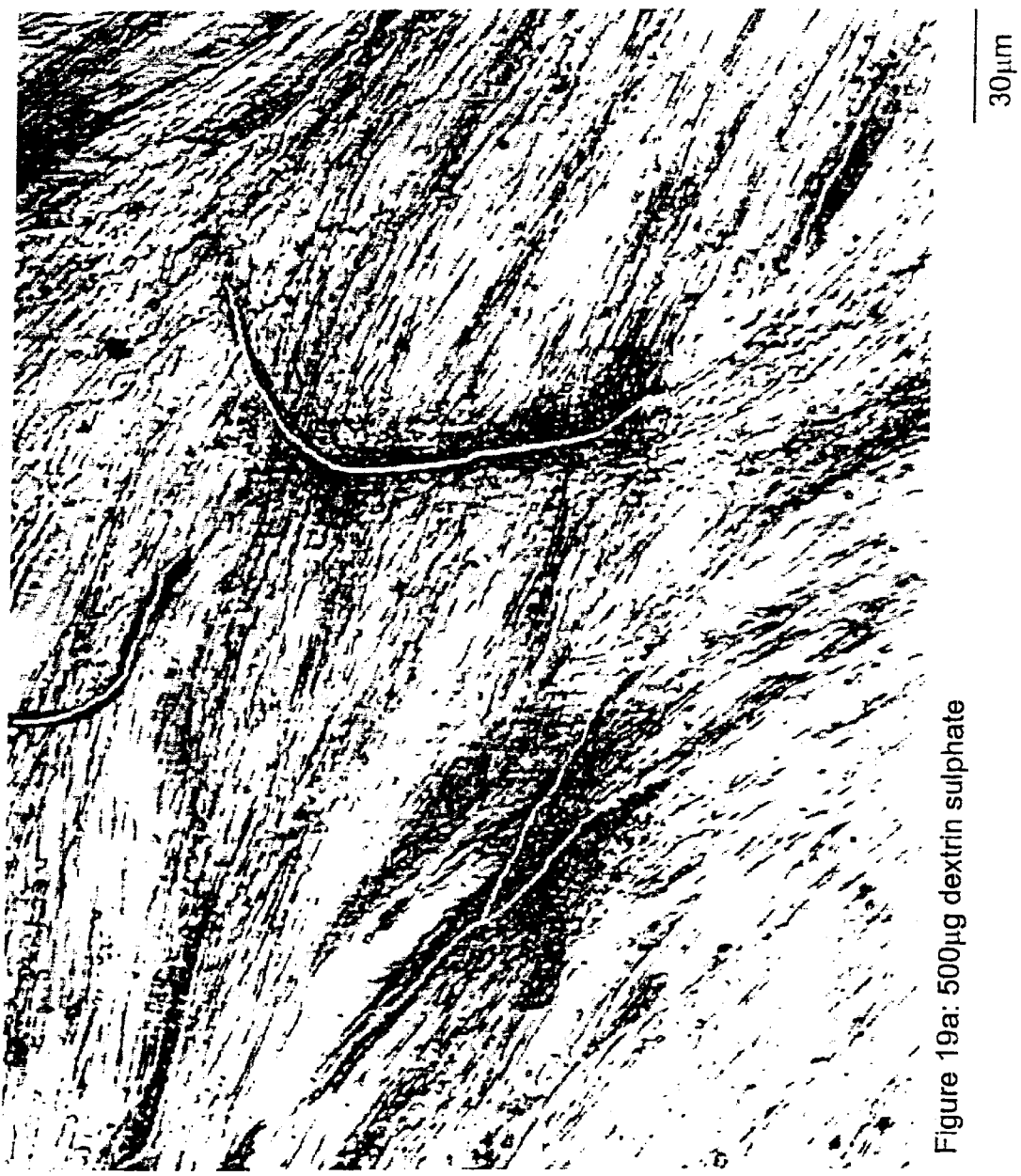
Figure 19a: 500μg dextrin sulphate

Figure 19b: 1000μg dextrin sulphate

TREATMENT OF ANGIOGENESIS DEPENDENT CONDITIONS WITH DEXTRIN SULPHATE

CROSS-REFERENCE TO RELATED APPLICATIONS

The present application claims priority under 35 U.S.C. §371 from PCT Application No. PCT/GB00/02799 (published under PCT Article 21(2) in English), filed on Jul. 24, 2000 which claims the benefit of Great Britain Application Serial No. 9917092.0, filed on Jul. 22, 1999, the disclosures of which are incorporated by reference herein in their entireties.

This invention relates to the treatment of diseases or disorders which are dependent on angiogenesis.

Angiogenesis, the development of new blood vessels from an existing vascular bed, is a complex multistep process that involves the degradation of components of the extracellular matrix and then the migration, proliferation and differentiation of endothelial cells to form tubules and eventually new vessels. Angiogenesis is important in normal physiological processes including, by example and not by way of limitation, embryo implantation; embryogenesis and development; and wound healing. Angiogenesis is however uncommon in healthy adults.

Angiogenesis is also involved in pathological conditions such as: ocular neovascular glaucoma; diabetic retinopathy; corneal graft rejection; vitamin A deficiency; Sjorgen's disease; acne rosacea; mycobacterium infections; bacterial and fungal ulcers; Herpes simplex infections; systemic lupus; rheumatoid arthritis; osteoarthritis; psoriasis; chronic inflammatory diseases (eg ulcerative colitis, Crohn's disease); hereditary diseases such as Osler-Weber Rendu disease and haemorrhagic teleangiectasia.

The vascular endothelium is normally quiescent. However upon activation endothelial cells proliferate and migrate to form microtubules which will ultimately form a capillary bed to supply blood to developing tissues and, of course, a growing tumour. A number of growth factors have been identified which promote/activate endothelial cells to undergo angiogenesis. These include, by example and not by way of limitation; vascular endothelial growth factor (VEGF); transforming growth factor (TGFb); acidic and basic fibroblast growth factor (aFGF and bFGF): and platelet derived growth factor (PDGF).

It is now well recognised that angiogenesis is a feature of a variety of diseases or disorders and that such conditions can be treated by administration of angiogenesis inhibitors. Many such inhibitors have been discovered. A number of endogenous inhibitors of angiogenesis have been discovered, examples of which are angiostatin and endostatin, which are formed by the proteolytic cleavage of plasminogen and collagen XVIII respectively. Both of these factors have been shown to suppress the activity of pro-angiogenic growth factors such as vascular VEGF and bFGF. Both of these factors suppress endothelial cell responses to VEGF and bFGF in vitro, and reduce the vascularisation and growth of experimental tumours in animal models.

Our PCT application WO 98/24421 relates to the treatment of patients suffering from highly vascular tumours which comprises administering dextrin sulphate to the patient. The mechanism of action of dextrin sulphate on highly vascular tumours was not known.

We have now found that dextrin sulphate is an angiogenesis inhibitor. New vessel formation is inhibited by a direct action effect of dextrin sulphate on endothelial cells. Its effect is to prevent endothelial cells coming together to form new vessels and then forming new blood vessels. Both processes are a prerequisite for the progression of an angiogenesis-dependent condition, such as the continued growth of a vascular tumour and of its metastatic lesions. The administration of dextrin sulphate to a patient can therefore provide a way of preventing angiogenesis and thereby arresting the progression of an angiogenesis-dependent condition.

Accordingly, the present invention provides a method of treating an angiogenesis-dependent condition, other than a highly vascular tumour, which comprises administering dextrin sulphate to the patient.

Considerable efforts has been directed towards the development of drugs which interfere with angiogenesis. One such group is sulphated polysaccharides. Their anti-angiogenic activity was first demonstrated using a combination of heparin and cortisone. This was followed by reports of several other sulphated polysaccharides which demonstrated anti-angiogenic activity in vitro. The most notable of these compounds was a naturally occurring sulphated polysaccharide-peptidoglycan (SP-PG) which is produced by the bacterium Arthrobacier sp (strain AT-25). SP-PG inhibited the growth of AIDS-associated Kaposi's sarcoma-derived spindle cells at concentrations that were not cytotoxic. It also blocked the angiogenesis which is induced by AIDS-Kaposi's sarcoma cells in nude mice. However, no clinical benefit was observed when SP-PG was administered intravenously to patients with AIDS-related Kaposi's sarcoma.

In a Phase I clinical trial of dextrin 2-sulphate in patients with late stage AIDS, we demonstrated that the direct administration of dextrin 2-sulphate into the lymphatic circulation using the intra-peritoneal route resulted in a significant and sustained fall in the viral load of HIV-1. No clinical or biochemical toxicity was seen even after the administration of several grams of the drug. During the course of the clinical trial, we noted the clinical regression of Kaposi's sarcoma in three patients and these observations were the subject of WO 98/24421. Here, we provide in vitro and in vivo data for a mechanism of action of the anti-angiogenic activity of sulphated dextrins which is independent of their anti-HIV-1 activity.

FIGURE LEGENDS

FIG. 1: Table to show the internalisation of dextrin 2 sulphate (D2S) and dextrin 6 sulphate (D6S) by different cell types.

FIG. 2: Table to show endothelial microtubule formation in the presence of sulphated dextrins.

FIG. 3: Graph to show the effect of sulphated dextrins on the proliferation of HUVECs induced by bFGF or VEGF was measured using a [$^3$H]-thymidine incorporation assay. There was no significant effect of either D2S or D6S on cellular proliferation. In similar experiments with the KSY-1 cell line, bFGF and VEGF did not increase cellular proliferation, and sulphated dextrins had no effect (data not shown).

Figure 4:
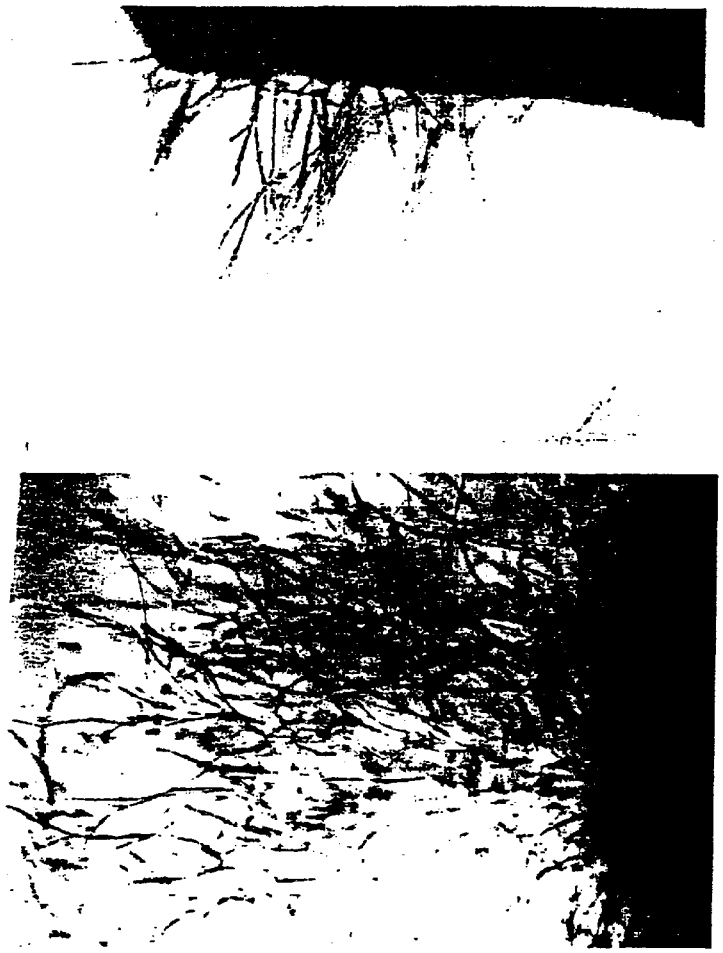

FIG. 4: The photomicrographs show new blood vessel formation at day 22 (×40 magnification).
  (a) vessel cultured in Medium 199 alone; score=3
  (b) vessel cultured in Medium 199 and D2S (100 μg/ml); score=1.

Figure 5:
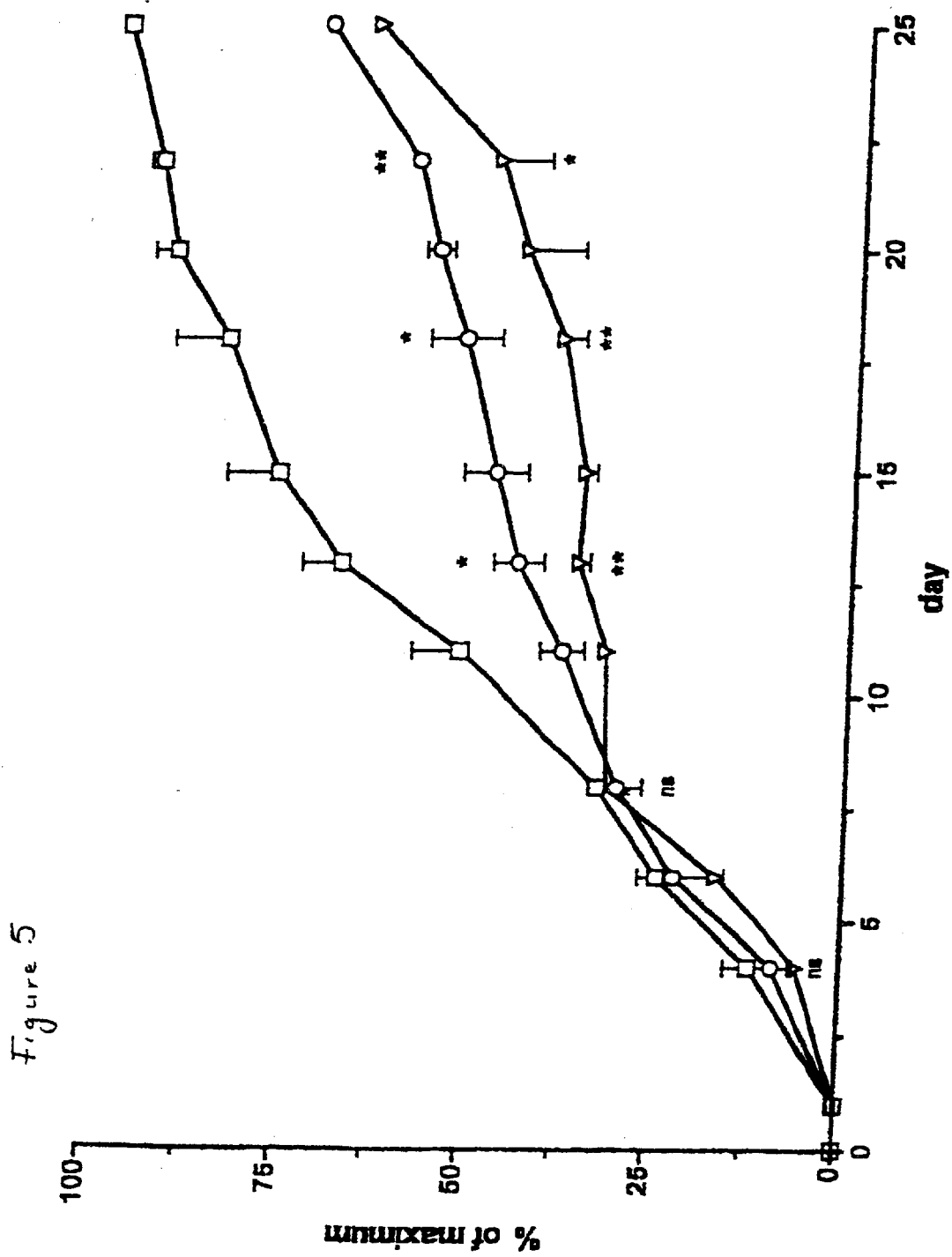

FIG. 5: Graph to show dextrin 2-sulphate (O) and dextrin 6-sulphate (∇) reduced the rate of new vessel formation in an in vitro angiogenesis assay model when compared to media alone (□). Compounds were tested at a final concentration of 100 μg/ml. The degree of new vessel formation was quantified blind twice a week using a visual analog scale in which 0=no growth, 1=minimal new vessel formation, 2=significant new vessel formation, and 3=dense new vessel formation. An angiogenesis score was derived from each count by dividing the total score (i.e. the sum of all the wells) by the maximum possible score and then expressing the result as a percentage. This graph is representative of 3 experiments with a total of 20 wells/plate/experiment for each compound tested.

p values:

ns:p>0.05.

*: p<0.05.

** p<0.01.

Figure 6:
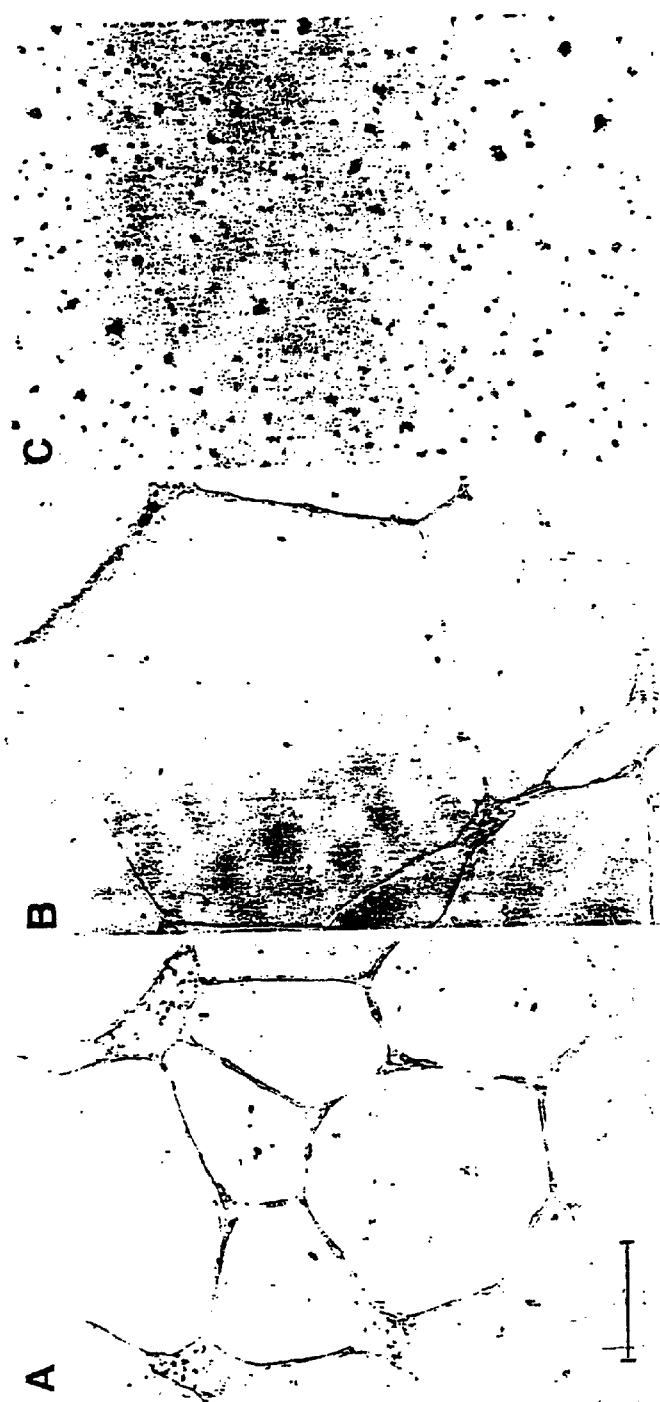

FIG. 6: The photomicrographs show endothelial microtubule formation in the presence of sulphated dextrins (×40 magnification). A visual analogue scale was used to determine the extent of tube formation and scored on a scale from 0 (all cells remain single) to 4 (all cells involved in tubular structures) as previously described (ref: 1,14). Space bar= 100 microns.

(A) Control well in the presence of dextrin (100 μg/ml), (B) D2S present at 200 μg/ml, (C) D6S present at 100 μg/ml.

Figure 7:
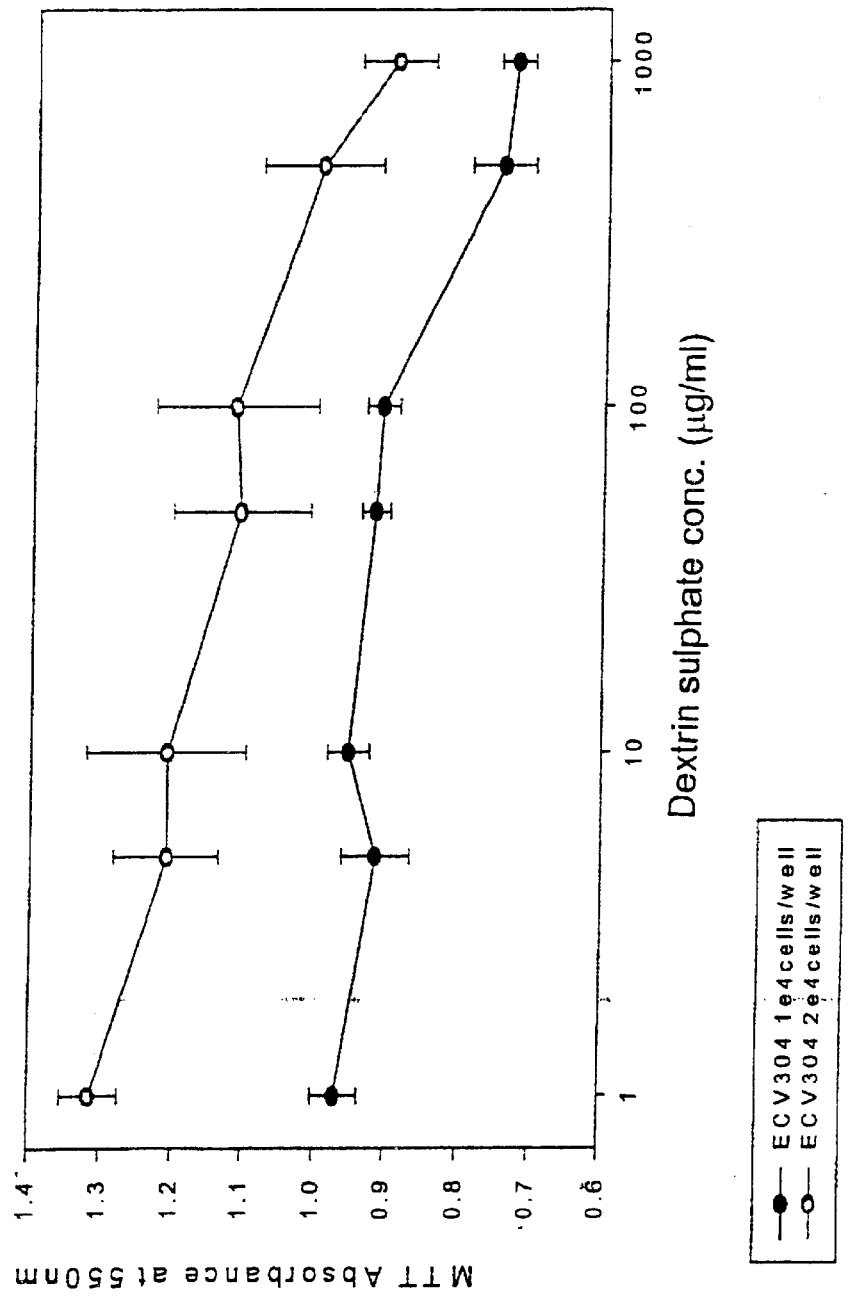

FIG. 7: Graph to show the effect of dextrin sulphate batch on the in vitro growth of ECV304 cells (Experiment 1).

Figure 8:
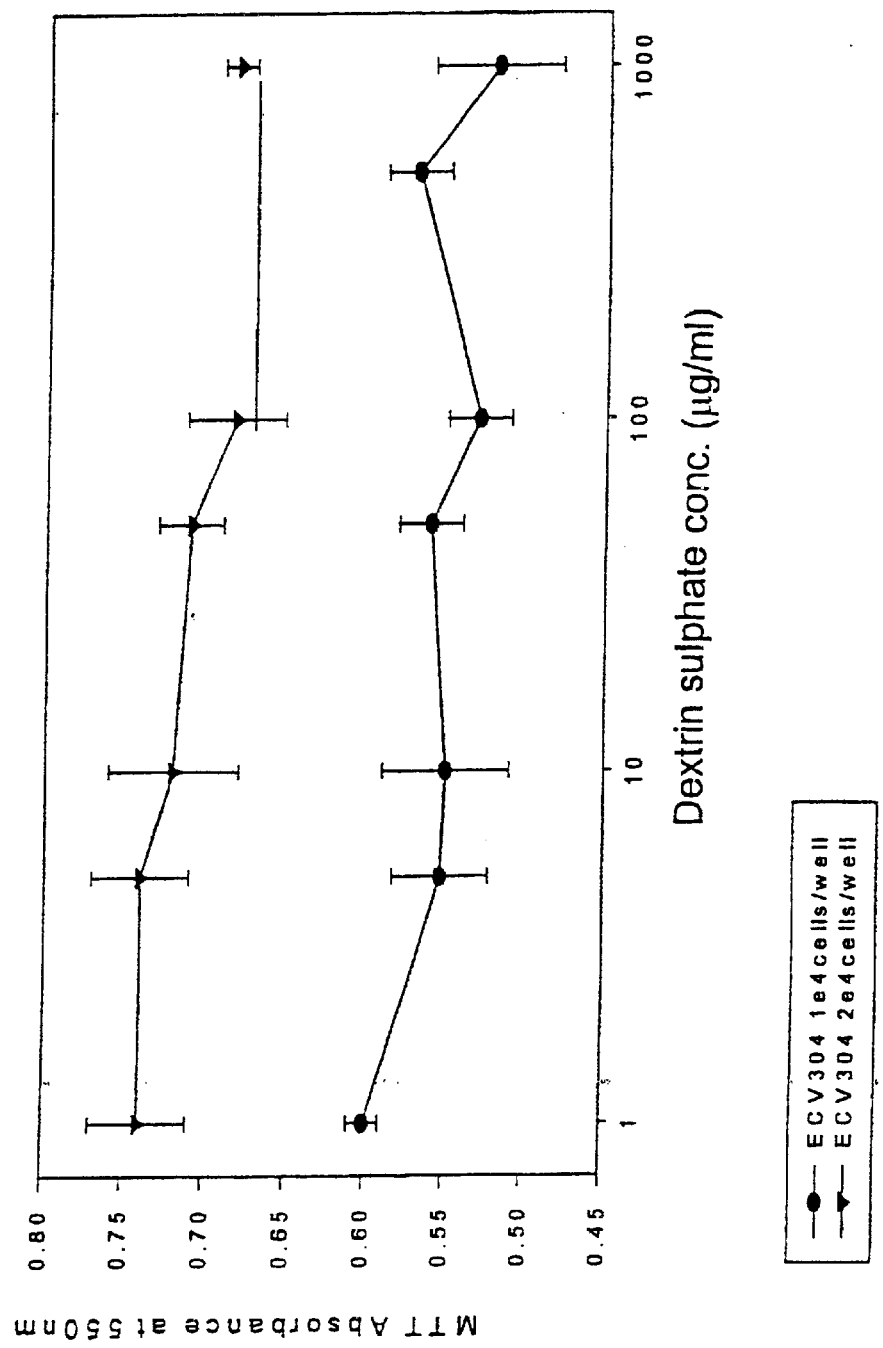

FIG. 8: Graph to show the effect of dextrin sulphate on the in vitro growth of ECV304 cells (Experiment 2).

Figure 9:
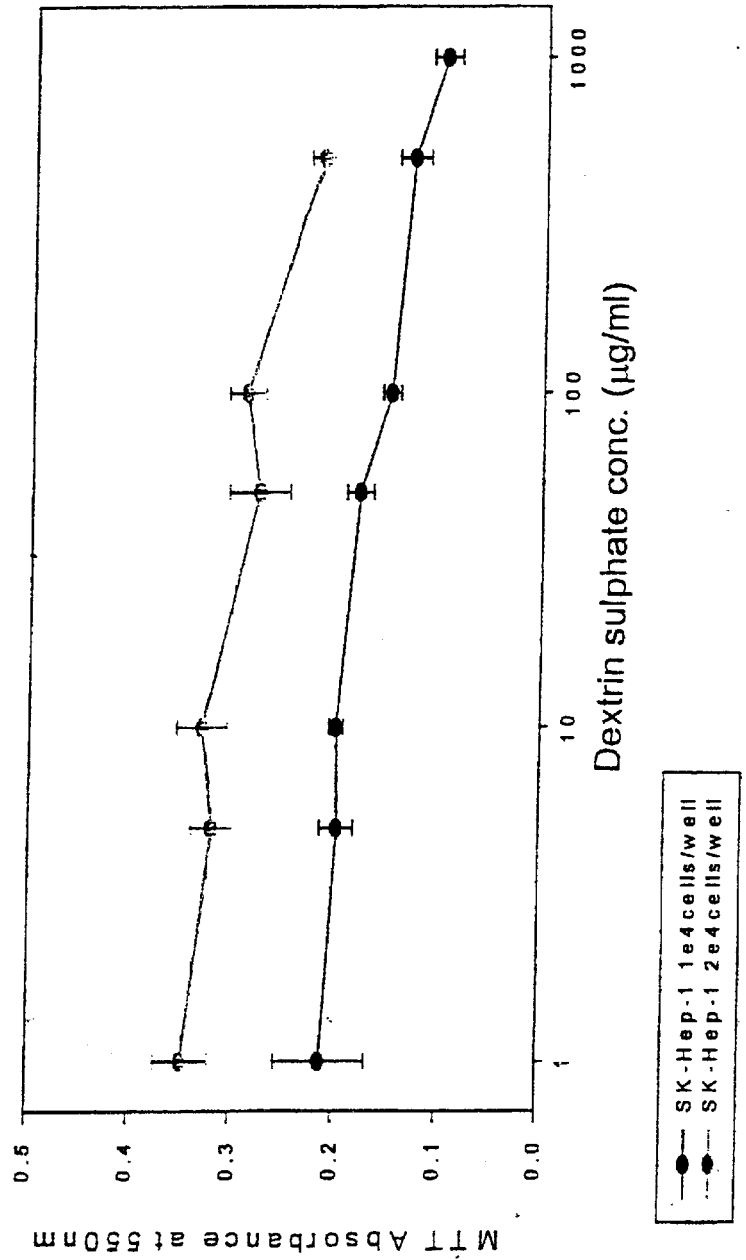

FIG. 9: Graph to show the effect of dextrin sulphate on the in vitro growth of SK-HEP-1 cells (Experiment 1).

Figure 10:
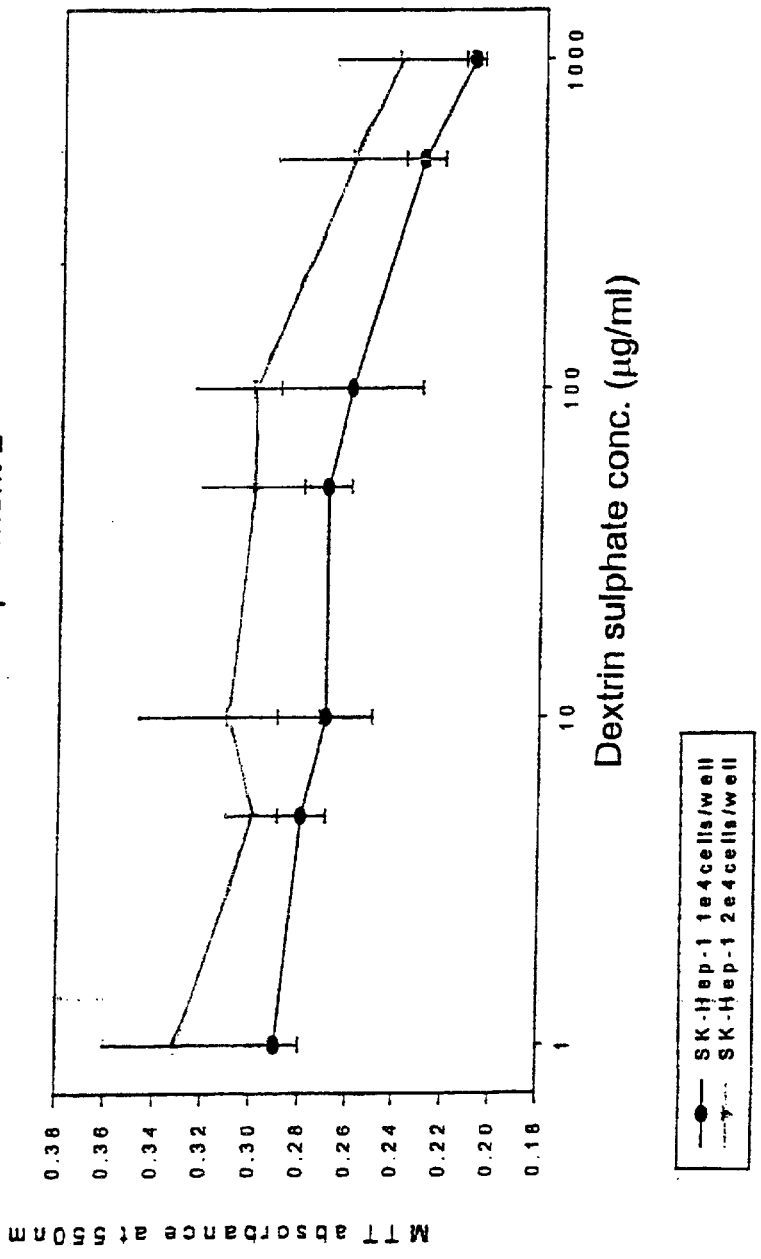

FIG. 10: Graph to show the effect of dextrin sulphate on the in vitro growth of SK-HEP- 1 cells (Experiment 2).

FIG. 11: Table to show the effect of dextrin sulphate on in vitro inhibition of endothelial-like cell lines (FK-HEP-1 and ECV304).

FIG. 12: Table to show mean angiogenesis measurements.

FIG. 13: Graph to show the effect of dextrin sulphate on HUVEC tubule number.

Figure 14:
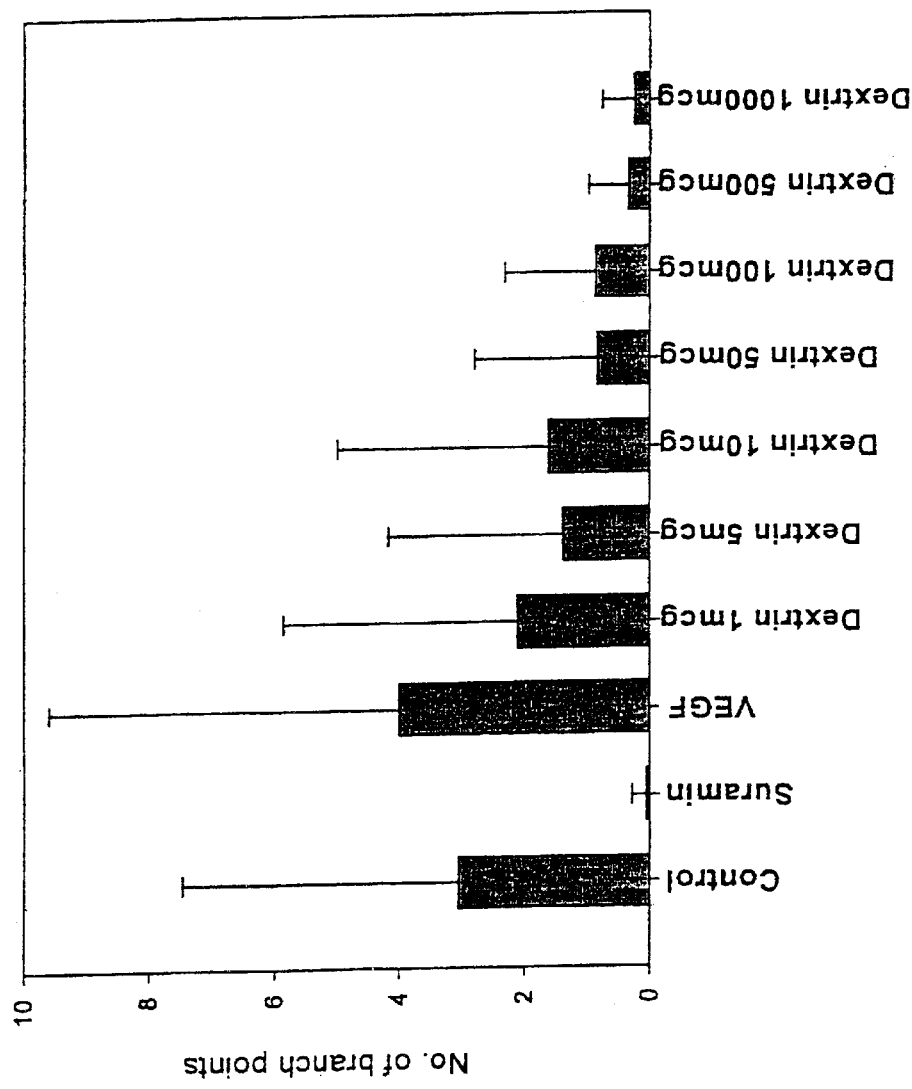

FIG. 14: Graph to show the effect of dextrin sulphate on the branch points of HUVEC tubules.

FIGS. 15a to 19b show microscopic images and represent the effect of dextrin sulphate on microtubule formation.

FIG. 15a: shows the microscopic images for the control experiments using Sumarin d2 7.

FIG. 15b: shows the tubule development for the control experiments using VEGF dl 4.

FIG. 16a: shows the microscopic images for the effect of dextrin sulphate at low concentration (0 μg d2 9).

FIG. 16b: shows the tubule development with dextrin sulphate at low concentration (1 μg d1 5).

FIG. 17a: shows the microscopic images for the effect of dextrin sulphate at concentration of 10 μg dl 2.

FIG. 17b: shows the tubule development with dextrin sulphate at concentration of 5 μg dl 1.

FIG. 18a: shows the microscopic images for the effect of dextrin sulphate at medium doses (50 μg dl 1).

FIG. 18b: shows the tubule development with dextrin sulphate at medium doses (100 μg dl 4).

FIG. 19a: shows the microscopic images for the effect of dextrin sulphate at high doses (500 μg dl 4).

FIG. 19b: shows the tubule development with dextrin sulphate at high doses (1000 μg d2 1).

Figure 20:
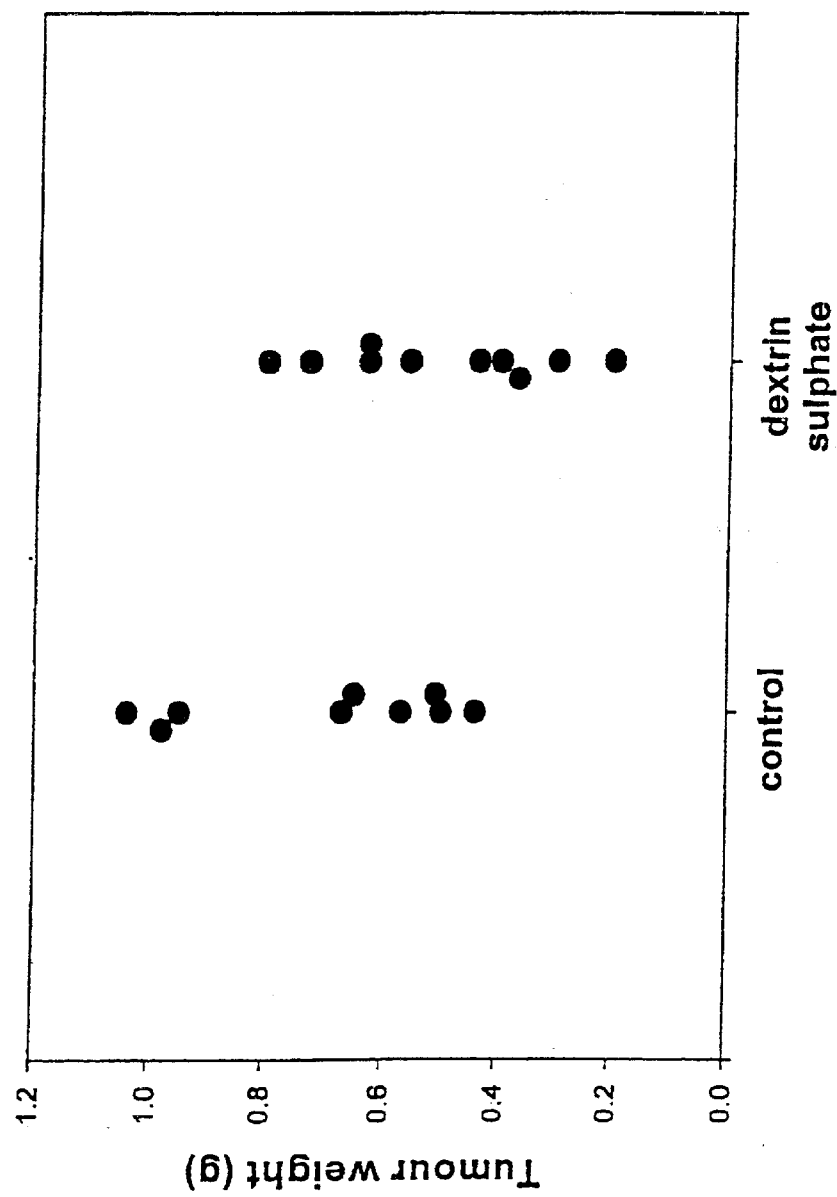

FIG. 20: Graph to show the effects of dextrin sulphate on individual tumour weights.

Figure 21:
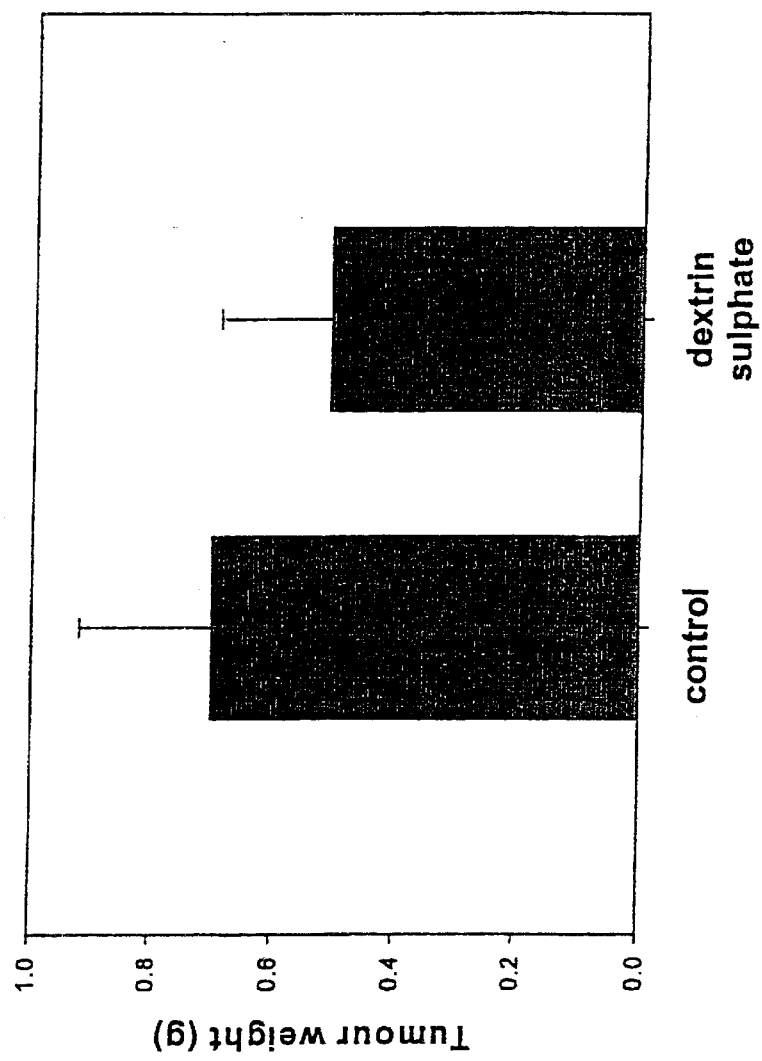

FIG. 21: Graph to show the effect of dextrin sulphate on mean final tumour weight.

EXAMPLE 1

Bovine plasma thrombin, bovine plasma fibrinogen, ε-amino-n-caproic acid, succinic anhydride, carbonyl diimidazole, biotin hydrazide and fast red/napthol substrate were purchased from Sigma (Poole, UK). Dimethylformainide and dimethylaminopyridine were from Adrich (Gillingham UK) and diethyl ether from BDH Merck (Lutterworth, UK). Clinical grade, endotoxin free, dextrin 2-sulphate, dextrin 6-sulphate, dextrin 2,6 sulphate (ML 95/50) and dextrin were obtained from ML Laboratories (Wavertree, UK). Medium MCDB 131, Medium 199, Hanks balanced salt solution, foetal calf serum, penicillin, streptomycin and L-glutamine were from Life Technologies (Paisley, Scotland).

We have previously shown that [$^3$H]-dextrin 2-sulphate binds to HPB-ALL cells in a specific and saturable manner with a dissociation constant (Kd) of 82±14 nM and a Bmax of 4.8±0.3 pmol/10$^6$ cells. CEM, C8166 and H9 cells had similar Kd values for the binding of [$^3$H]-D2S. We have also shown that [$^3$H]-dextrin 2-sulphate binds to HeLa cells (an immortalised endothelial cell line) with a similar Kd of 107±12 nM and a Bmax of 4.1±0.2 pmol/10$^6$ cells; n=9, p<0.05.

Dextrin 2-sulphate accumulated in the peritoneal macrophages and mesothelial cells of treated patients, but not in any other cell type found in the peritoneal cavity or in the peripheral blood of these patients. In subsequent in vitro experiments, different cell types were cultured with 100 μg/ml of endotoxin free D2S, 100 μg/ml dextrin or 100 μg/ml biotinylated dextrin, or 100 μg/ml of dextrin 6 sulphate, for up to 4 weeks (FIG. 1). The cells were then stained with 1,9 dimethylmethylene blue which detects sulphated glycosaminoglycans (Blysan, Biocolor, Belfast), or alkaline phosphatase-conjugated streptavidin and fast red/napthol which detects intracellular biotinylated sulphated dextrins.

Human umbilical vein endothelial cells (HUVEC's) were also harvested from umbilical cords by digestion with collagenase type II and cultured in 1% gelatin coated tissue culture flasks in Medium 199 supplemented with 20% fetal bovine serum, 100 IU/ml penicillin, 0.1 mg/ml streptomycin, 2mM L-glutamine, 10 U/ml heparin and 20 μg/ml endothelial cell growth supplement. The KS Y-1 cell line which was established from the pleural effusion of a patient with AIDS-associated Kaposi's sarcoma was also studied. It was CD34 and CD31 positive confirming it as being of endothelial origin.

After 3 weeks of continuous culture, D2S and D6S were only found to accumulate in peritoneal macrophages.

The cells were maintained in the presence of the sulphated dextrin for up to 4 weeks.

As sulphated dextrins did not accumulate in human umbilical vein endothelial cells (HUVECs) or in the Kaposi's sarcoma cell line, KSY-1, we determined whether sulphated dextrins could interfere with the normal growth of these cells by an action at the level of the cell surface. Our previous studies of peripheral blood mononuclear cells and monocyte-derived-macrophages have shown that D2S binds to the cell surface in a specific and saturable manner with a dissociation constant of 82±14 nM. Furthermore, concentrations up to 250 μg/ml did not affect cell count, cell viability, cell proliferation or metabolic activity when compared to cells cultured in the absence of each compound.

Neither dextrin nor sulphated dextrins affected the rate of cell division of HUVEC's or KSY-1 cells over a 7 day period as determined by twice weekly cell counts. Cell viability remained >95% at all times as determined by Trypan blue exclusion. The effect of sulphated dextrins on the growth of HUVEC's and KSY-1 cells which were being cultured in the presence of basic fibroblast growth factor (bFGF) or vascular endothelial growth factor (VEGF) was also determined.

For these experiments, HUVECs ($5 \times 10^3$/well) were suspended in Medium M199 containing 10% FCS, 2 mM L-glutamine, 100 Iu/ml penicillin and 0.1 mg/ml streptomycin. After 24 h, the media was replaced with fresh media containing either D2S (100 μg/ml) or D6S (100 μg/ml) for 1 h following which either bFGF (10 ng/ml) or VEGF (20 ng/ml, Preprotech, Rocky Hill, N.J.) were added. These concentrations of VEGF and bFGF were chosen because they have been shown to cause HUVECs to proliferate. [$^3$H]-thymidine (1 mCi/ml, Amersham Pharrnacia, Bucks, UK) was added 48 h later and the cells cultured for a further 16 h. Cells were harvested using an automated Betaplate 96 well harvester (Wallac Oy, Turku, Finland) and the radioactivity counted using a Betaplate liquid scintillation counter. Sulphated dextrins did not alter the rate of proliferation of HUVECs or KSY-1 cells as determined by cell counts and [$^3$H]-thymidine incorporations, even when exogenous bFGF or VEGF were added (FIG. 3).

EXAMPLE 2

Blood vessels (approximately 1–2 mm diameter) were excised from the apical surface of human placentas within 6 h of an elective Caesarean birth. Use of the placentas for these studies were approved by the Ethics Committee of Hammersmith Hospitals Trust, London. The blood vessels were placed in Hank's balanced salt solution and cut into 1–2 mm fragments using fine dissecting forceps and iridectomy scissors. Residual clots were removed and the blood vessels then soaked in Hank's balanced salt solution.

The effect of each compound on new blood vessel formulation was determined by culturing the blood vessels within a fibrin clot in 24-well tissue culture plates. Thirty μl of bovine thrombin (50 NIH U/ml in 0.15 M sodium chloride) was added to each well followed by 1 ml/well of 3 mg/ml bovine fibrinogen in Medium 199. The thrombin and fibrinogen were rapidly mixed and a blood vessel fragment placed in the centre of the well. Fibrin gel formation occurred rapidly and left the vessel suspended within the gel. One ml/well of Medium 199 supplemented with 20% foetal calf serum, 250 IU/ml penicillin and 250 U/ml streptomycin was then added to each well. ε-arnino-n-caproic acid was also added (300 μg/ml) for the first 4 days and twice weekly thereafter (50 μg/ml) in order to prevent dissolution of the fibrin clot. The vessels were cultured at 37° C. in a humidified incubator for 25 days with the media being changed twice weekly.

The degree of new vessel formation was quantified blind twice a week by three different observers using a visual analogue scale in which 0=no growth, 1=very little new vessel formation, 2=significant new vessel formation and 3=dense new vessel formation. An angiogenesis score was derived from the counts undertaken for each well by dividing the total score by the maximum score possible and then expressing the result as a percentage. On each of 3 separate occasions, each compound was tested in 20 replicate wells. Experiments in which blood vessels were cultured in MCDB 131 (ie serum free media) showed that serum factors were not necessary for new blood vessel formation. Some of the fibrin clots were fixed overnight in 10% formalin, paraffin embedded, sectioned for histology and then stained for the endothelial cell markers Factor VIII and CD31. Results are expressed as the mean±sem. A students t-test was used to determine the level of significance.

Over the 3 week course of the assay, a complex arcade of microvessels emerged from the cut section of the blood vessel embedded within a fibrin clot. Very little growth of new vessels was seen from those areas of the vessel which had not been sectioned. The first blood vessels appeared by day 4 and were usually blunt-ended. Over the next 18 days, they went on to branch and give rise to complex arcades of vessels. Growth was rapid for the first 2 weeks and then slowed considerably. These new vessels were lined by endothelial cells as demonstrated by positive immunohistochemistry for Factor VIII and CD31.

FIGS. 4 and 5 show the effect of dextrin 2-sulphate and dextrin 6-sulphate on new vessel formation. There was no difference between vessels cultured in media as compared to vessels cultured in media containing dextrin (100μg/ml); (40 wells; 2 experiments; p=0.9 on day 18). In contrast, there was a significant reduction in the number of new vessels which formed when dextrin 2-sulphate (100μg/ml) was present. This was first seen at day 13 (p=0.02), and the difference was still present at day 22 (p=0.03). Dextrin 6-sulphate also caused a significant decrease in new vessel formation. This was first seen at day 13 (60 wells; 3 experiments; p=0.004) and was still present at day 22 (p=0.002).

EXAMPLE 3

Kubota et al reported that human umbilical vein endothelial cells undergo morphological differentiation with tube formation when cultured on a reconstituted gel composed of basement membrane proteins (Matrigel; Beckton-Dickinson). This has parallels with the in vivo situation where endothelial cells line the lumen of blood vessels and are in contact with the extracellular matrix of basement membranes which is composed of collagen IV, heparin sulphate proteoglycan and the glycoproteins laminin and nidogen/entactin.

Due to the ability of basement membranes to stimulate differentiation, cells plated onto the gel attach rapidly. Within one to two hours, elongated processes are observed. After eight hours, the endothelial cell cultures show abundant networks of branching and anastomosing of cords of cells. By light microscopy, most of these cords showed a central translucent structure along their long axis suggesting the presence of a lumen. By eighteen hours, the endothelial cells have formed an interconnected network of anastomosing cells which, by low power light microscopy, have a honeycomb appearance. The tube like structures formed by endothelial cells on Matrigel persist for several days. With time, the network starts to detach from the Matrigel with viable endothelial cells appearing in the culture media. The formation of the tube structures is not dependent on extracellular growth factors or the presence of heparin in the culture media.

The formation of tubes appears to be relatively specific for endothelial cells because neither human dermal fibroblasts nor human smooth muscle cells form tubes when cultured on Matrigel. The endothelial cells cultured on Matrigel retain Factor VIII reactivity and are metabolically active as indicated by their uptake of acetylated low density lipoproteins. Furthermore, after more than one week in culture, the human umbilical vein endothelial cells grown on Matrigel show no increase in their cell number, as compared to cells grown on fibronectin which show a fourfold increase in cell number.

Ultrastructural EM studies have confirmed that the anastomosing cytoplasmic extensions of the morphologically differentiated endothelial cells contain a lumen which is completely encircled by one or two endothelial cells in cross section. The lumen contains various amounts of degenerated cytoplasm, suggesting that very rapid remodelling of the cell takes place during the tube formation. Viability studies of endothelial cells cultured on Matrigel do not indicate that cell death plays an important role in tube formation. Moreover, these differentiated cells retain the characteristic Weibel-Palade bodies of endothelial cells.

The endothelial microtuble formation assay was performed by isolating human umbilical vein endothelial cells from umbilical cords within 6 h of delivery by caesarean section. The umbilical vein was cannulated and 0.1% collagenase in phosphate buffered saline was introduced and incubated for 20 minutes. The endothelial cells liberated by the collagenase were obtained by washing the umbilical vein with Medium 199. The cells were washed three times with Medium 199 and then cultured in tissue culture flasks coated with fibronectin. Growth media consisted of Medium 199 with 20% foetal bovine serum, 30 µg/ml epidermal cell growth supplement, 10 IU/ml heparin, 100 IU/ml penicillin, 100 µg/ml streptomycin and 2 mM L-glutamine. Human umbilical vein endothelial cells were passaged at confluence after treatment with trypsin-EDTA. All cells were used at passages 3 to 6.

Aliquots of Matrigel were dispensed into 35 mm diameter tissue culture dishes on ice and then incubated at 37° C. for 10 min to allow the gel to set. Dilution series of D2S and D6S were prepared in HUVEC growth medium and added to the dishes. HUVECs at passage 3 to 6 were harvested using trypsin and suspended in growth medium at a density of $2-3 \times 10^5$ cells/ml. One ml aliquots of the cell suspension were added to the plates containing the sulphated dextrins and incubated at 37° C., 5% $CO_2$. At various time points from 8–24 hours, the plates were examined and scored using a published scheme from 0–4, where 0=all adherent cells remain single, and 4=all adherent cells involved in tubular structures. New vessel formation was quantified blind by three different observers at 18 h. The within-observer and between-observer variability was <10%. n=3. The results from dextrin 2-sulphate and dextrin 6-sulphate are shown in FIGS. 2 and 6.

A bisulphated dextrin sulphate (ie: endotoxin free dextrin 2,6-sulphate; ML 95/50) was also tested in this assay. This molecule consists of one sulphate in the 2' position on each glucose molecule with approximately 30% of the glucose molecules also having a sulphate in the 6' position. Its anti-angiogenic activity was more than that seen with D2S but less than that seen with D6S. This showed that having more than one sulphate per glucan molecule increases the anti-angiogenic activity of sulphated dextrins.

The in vitro model of angiogenesis used for testing sulphated dextrins fulfilled the two hallmarks of angiogenesis, ie: endothelial cell proliferation and capillary sprouting. When similar in vitro assays have been used to test other sulphated polysaccharides, the data has been difficult to interpret because the compounds did not first undergo detailed chemical characterisation. Our in vitro observations show that sulphated dextrins inhibit new vessel formation by normal endothelial cells and that this prevents new blood vessel formation; ie: angiogenesis.

In this respect, it is interesting to review the studies of Nakamura et al who showed that SP-PG inhibited the angiogenesis which was seen after the subcutaneous inoculation of AIDS-KS cells in nude mice. However, they had to administer 250 mg/kg/day in order to abolish angiogeneisis. Such a dose could never have been achieved in patients and probably explains why an inhibition of angiogenesis was not seen in a subsequent clinical trial when the drug was administered intravenously. In contrast, we have administered a dose of ≈2 mg/kg/day and observed a significant clinical effect on early Kaposi's sarcoma lesions without any associated toxicity.

In a recent report it was shown that sulphated dextrins did not interfere with the growth of but did inhibit the morphological differentiation of epithelial cells (Thornton et al, Anti-microbial Agents and Chemotherapy 43, 2528–2533, 1999). The results of the placental angiogenesis assay show that dextrin sulphate inhibits new vessel formation and differentiation of the HUVEC cell line.

EXAMPLE 4

The effect of dextrin sulphate on in vitro proliferation of 2 endothelial cell lines and vessel formation of the HUVEC endothelial cell line was assessed.

SK-HEP-1 is a human liver adenocarcinoma with endothelial morphology and ECV304 is a human urinary bladder carcinoma with endothelial-like characteristics. Both cell lines were obtained from the ECACC. HUVEC was provided as a growing culture by TCS Biologicals.

Cells were grown and prepared in RPMI medium containing 10% FCS and 2mM glutamine. For the in vitro assays, cells were harvested with 0.025% EDTA, washed in the culture medium and plated into 96-well plates at $5 \times 10^3$ and $1 \times 10^4$ cells/well in a volume of 100 µl. After 24 hours, to allow for cell adherence, the medium was replaced with fresh medium containing dextrin sulphate at concentrations of 0, 1, 5, 10, 50, 100, 500, 1000 µg/ml. After 48 hours, proliferation was assessed by methyl thiazol tetrazolium (MTT) uptake as follows:

MTT (Sigma) was added to the wells in a 50 µl volume at a concentration of 1mg/ml. After 4 hours incubation the insoluble formazan crystals were solubilised by the addition of 75 µl DMSO/well and the absorbance measured at 550 nm. The MTT assay has previously been shown to correlate with direct cell counts for a number of GI epithelial cell lines (Watson et al, Anti-cancer drugs, 1994; 5, p 591–597).

The effect of sulphated dextrin on vessel formation of the HUVEC cell line was performed by the use of the TCS Biologicals Human Angiogenesis Model. The assay is supplied as a growing culture of the HUVEC cell line together with culture matrix and additional human cells present (the exact nature of the cells is not known) at the earliest stages of tubule formation in a 24-well format. The positive control reagent was a standard stock solution of VEGF and the negative control was Suramin. After removing the well seals, the cultures were examined for cell morphology to confirm their viability.

Growth medium was provided with the kit and was used to make up the sulphated dextrin at concentrations ranging from 0–1000 µg/ml. The existing medium was aspirated from the wells and replaced with medium containing the dextrin sulphate concentrations in a 0.5ml volume. This was placed at 37° C., in a 5% $CO_2$ containing atmosphere. This was repeated on days 4, 7 and 9.

Between days 7–11 cultures were fixed by the enclosed fixative and stained with the mouse monoclonal anti- PECAM-1 antibody at a 1:4000 dilution (present in blocking buffer). 0.5ml of diluted antibody was added per well and incubated for 60 minutes at 37° C. The secondary antibody (goat anti-mouse lgG alkaline phosphatase conjugate) was diluted 1:500 in blocking buffer and added to the wells after washing for 60 minutes at 37° C. After washing the plate the substrate was prepared; BCIP/NBT tablets were dissolved in distilled water and added to the wells. Following incubation for 5–10 minutes the wells were washed and were imaged using the Leica Qwin image analysis software package.

Dextrin sulphate was assessed in two separate experiments. All experiments were performed with two different cell-seeding concentrations. Dextrin sulphate induced moderate levels of inhibition (See FIGS. 7, 8, 9 and 10). To compare between cell lines and experiments, the level of inhibition achieved at the highest concentration evaluated (1000 $\mu$g/ml) was calculated as was the significance from the untreated control. (See FIG. 11).

The SK-HEP-1 cell line was inhibited to a greater extent than the ECV304 cell line, with dextrin sulphate inducing ~65% inhibition at the lower cell concentration. Inhibition at the higher cell concentration was not as great.

The level of inhibition that was shown with the ECV304 cell line was in the range of 11–33%. There was no difference between the level of inhibition at the 2 cell concentrations.

The results of the effect of dextrin sulphate on tubule formation is given in FIGS. 12, 13 and 14.

The tubule distance was not represented graphically as there was no discrimination within the experiment between positive and negative controls. With respect to tubule number, Suramin induced a significant inhibitory effect (51%, p<0.0001, Student's t-test) when compared to the vehicle control whereas VEGF induced a significant elevation (174%, p<0.0001). The effect of dextrin sulphate on branch point number was concentration-dependant, with significant stimulation occurring at the lowest concentrations (1 and 5 $\mu$g/ml, 120% and 115% of control). Inhibition was however shown at concentrations greater than 10 $\mu$g/ml (26%, 48%, 53% and 68% inhibition, at concentrations of 50, 100, 500 and 1000 $\mu$g/ml, respectively). Suramin significantly inhibited branch points (98% inhibition, p<0.0001) whereas VEGF just significantly elevated branch points (131%, p<0.05). All concentrations of dextrin sulphate significantly reduced tubule branch points from 31% with 1 $\mu$g/ml down to 93% with 1000 $\mu$g/ml (significance shown on FIG. 12). Microscopic images are shown in FIGS. 15, 16, 17 18 and 19.

Dextrin sulphate inhibited the basal growth of the endothelial-like cell lines, SK-HEP-1 and EVC304 as assessed by the MTT assay. The inhibitory effects were seen at concentrations >100 $\mu$g/ml. Seeding cells at a higher concentration did not appear to increase the magnitude of the inhibitory effect, indicating the action is likely to be cytostatic rather the cytotoxic. SK-HEP-1 was more sensitive to the growth-inhibitory effects of the sulphated dextrin.

The proliferation of HUVEC cells is known not to be directly inhibited by dextrin sulphate in vitro (Thornton et al, 1999). However the effect of dextrin sulphate was evaluated on the angiogenic characteristics of HUVEC cells in a mixed cell culture in the presence of ECM. VEGF and Suramin were used as positive and negative controls, respectively, and affected tubule formation and branch points in the correct direction. Dextrin sulphate induced low but significant stimulation of tubule number at the lower concentrations but at the highest concentration of 1000 $\mu$g/ml induced 68% inhibition. The level of inhibition of tubule number at 100 $\mu$g/ml (48%) was comparable to that reported in the study by Thornton et al.

Dextrin sulphate induced an inhibitory effect on branch point number at all concentrations evaluated.

Sulphated dextrin inhibited the growth of 2 endothelial like cells lines in an in vitro assay and inhibited tubule number and branch points of the HUVEC cell line in an angiogenesis assay.

EXAMPLE 5

The ability of dextrin sulphate to inhibit the in vivo growth of the well-vascularised human colorectal xenograft AP5LV was investigated.

Dextrin sulphate, 10 mg/kg in 1ml icodextrin was administered every second day to two male SCID mice. Dosing continued for 14 days.

The cell line evaluated, AP5LV, is a variant of an established human colorectal cell line, derived originally from a patient's primary tumour. AP5LV cells have been selected for their ability to both colonise the lungs following intravenous injection and to spontaneously metastasise to the lungs following injection of the cells into the peritoneal muscle wall. AP5LV cells were maintained in vitro in RPMI 1640 culture medium (Gibco, Paisley, UK) containing 10% (v/v) heat inactivated foetal bovine serum (Sigma, Poole, UK) at 37° C. in 5% $CO_2$ and humidified conditions. Cells from semi-confluent monolayers were harvested with 0.025% EDTA, washed twice in the culture medium described above, and re-suspended at $5\times10^6$/50 $\mu$l in sterile phosphate buffered saline, pH 7.4(PBS).

The mice were anaesthetised using Hypnorm(Roche)/Hyponovel(Janssen) and the cell suspension injected into the peritoneal muscle wall of 20 male SCD mice. Mice were electronically tagged for identification purposes (RS Biotech, Tracker), and randomly allocated to two experimental groups (see below). The treatment regime was initiated on day 1 and continued every other day until termination on day 38.

At termination the peritoneal muscle wall tumours were excised and weighed, half being snap frozen and half Formalin fixed. The lungs were also removed and Formalin fixed for evaluation of metastatic tumour burden.

Mice were weighed throughout the study.

Group 1, n=10 males—4% Icodextrin, 1ml i.p. every second day Group 2, n=10 males—dextrin sulphate 10 mg/kg in 4% Icodextrin, 1ml i.p. every second day The final tumour weights are shown in FIG. 20 (tumour weights for individual mice) and FIG. 23 (mean tumour weights for each experimental group). Dextrin sulphate induced a 28% reduction in final tumour weight which just failed to reach significance (p=0.065, Student's T-test).

The dose of dextrin sulphate chosen for the initial therapy study just failed to induce a significant effect on the final tumour weights of the human colorectal xenograft, AP5LV. This may reflect the fact that n=9/10 mice per group were not high enough to show significance at this level of inhibition. There was no toxicity with this dose.

EXAMPLE 6

Dextrin sulphates are known compounds. They are produced by sulphation of dextrins, which are mixtures of glucose polymers produced by hydrolysis of starch. These glucose polymers have a wide range of polymerisation. The degree of polymerisation (DP) varies from 1 (the monomer, glucose) up to very high values, for example up to a hundred thousand or more glucose units.

Typically, the direct result of hydrolysing a starch is a dextrin containing a high proportion of polymers of relatively low molecular weight and might for example contain up to 60% by weight of glucose polymers of DP less than 12. The dextrin sulphates used in the present invention can have a wide range of composition, but are preferably derived from dextrins containing at least 50% by weight, preferably more than 90%, of glucose polymers greater than 12, and/or containing less than 10%, preferably less than 5%, by weight of glucose polymers of DP less than 12. The weight average molecular weight of the dextrin may, for example, be from 10,000 to 35,000, preferably 15,000 to 25,000. (The technique used to determine the molecular weight of the dextrin is high-pressure liquid chromatography using chromatographic columns calibrated with dextrin standards, as designated by Alsop et al, J Chromatography 246, 227–240, 1989). Preferably, the dextrin contains nor more than 10%, preferably less than 5%, by weight of polymers of molecular weight greater than 40,000. The desired weight average molecular weight and polymer profile is achieved by subjecting to dextrin to fractionation, using known techniques, including solvent precipitation and membrane fractionation. Among the dextrins from which the dextrin sulphates suitable for use in the present invention can be derived are those described in European patent specifications Nos 115911, 153164 and 207676.

Dextrin sulphates have been previously used pharmaceutically. For example, British patent specification 871,590 discloses the use of certain dextrin sulphates as antilipaemic agents, and United States patent specification 5,439,892 discloses the use of certain dextrin sulphates as anti-HIV agents. These references also describe processes for the production of dextrin sulphates; their disclosures are incorporated herein by reference.

In the method of the invention the dextrin sulphate can be administered to the patient by any route, enteral or parenteral, at the discretion of the clinician. Intraperitoneal administration is particularly effective, but the dextrin sulphate can, for example, also be given orally, intravenously, or can be directly injected into lesions on a lesion by lesion basis, or can be topically applied. The dosage level is to be determined by the clinician.

Dextrins can be sulphated in the 2, 3 and 6 positions, and a fully sulphated dextrin therefore contains three sulphate groups per glucose unit. The dextrin sulphate used in the present invention may have any degree of sulphation, but preferably it contains at most two, more preferably from 0.5 to 1.5, sulphate groups per glucose unit. Also, the dextrin sulphate is preferably dextrin-2-sulphate, dextrin-6-sulphate or a mixture thereof.

A composition for use in administering dextrin sulphate intraperitoneally was prepared, in the form of a sterile aqueous solution containing:

| Dextrin sulphate | 100 | micrograms/ml |
| Glucose polymer mixture | 10 | grams/litre |
| Na | 132 | mmol/litre |
| Ca | 1.75 | mmol/litre |
| Mg | 0.75 | mmol/litre |
| Lactate | 35 | mmol/litre |

The dextrin sulphate was dextrin-2-sulphate, prepared as described in Example 3 of U.S. Pat. No. 5,439,892. The glucose polymer mixture, present in the solution as an osmotic agent, was the glucose polymer mixture described in Example 2 of European specification 153164; it contained 91.9% of polymers of DP greater than 12 and 7.9% of polymers of from DP 2 to 10, and had a weight average molecular weight of 23,700.

EXAMPLE 7

In the adult organism, endothelial cells proliferate at an extremely slow rate with turnover times which have been estimated to be years. Under certain physiological (eg: ovulation) and pathological considions (eg: wound healing, inflammation, tumour growth, rheumatoid arthritis, diabetic retinopathy and inflammatory bowel disease), new blood vessels grow rapidly from pre-existing capillaries by a sprouting process which is similar to embryonic angiogenesis. Physiological angiogenesis is therefore rare. Other forms of angiogenesis in the adult are almost always associated with a pathological disease process.

a) Inflammation and Angiogenesis

Whilst these two processes are separate, distinct and separable, they are nevertheless closely related. The histological appearance of chronic inflammation includes the presence of granulation-like tissue of which neovascularisation is a prominent feature. The marked increase in the metabolic demands of a tissue which is proliferating, repairing or undergoing hypertrophy have to be accompanied by a proportional increase in the capillary blood supply. This is an absolute requirement and it suggests several characteristics of angiogenesis. First, the vascular system must be able to respond rapidly to the increased needs of the tissue with an increase in its micro-vasculature. Secondly, the high metabolic cost of angiogenesis means that the process must be tightly controlled under basal conditions and that it should only occur when absolutely necessary. Thirdly, when such strict control is lost, an abnormal environment is created and this leads to disease.

Therefore, endothelial cells which arc normally quiescent become activated as part of the angiogenic response. When endothelial cells from the micro-vasculature are stimulated, they degrade their basement membrane and proximal extra-cellular matrix, migrate directionally, divide, and organise into functioning capillaries which are invested by a new basal lamina. These steps are not sequential. Rather they represent an orchestration of overlapping events which are necessary to try to return the injured tissue to the normal homeostatic state. In each of these steps of angiogenesis, there remain substantial gaps in our knowledge of the exact mechanisms involved.

The signal which initiates angiogenesis varies with the condition which triggers stimulation and angiogenesis and is thought to be organ specific. For example, platelet degranulation as well as proteolytic digestion of the extra-cellular matrix have been implicated because they occur rapidly after tissue injury and they do not require new protein synthesis. However, many cells can also be the source of angiogenic signals and they include tumour cells, fibroblasts, epithelial cells and endothelial cells.

Therefore, angiogenesis, as defined by the growth of new capillaries from pre-existing vessels, is a fundamental biological process which is at the core of many physiological and pathological processes. In chronic inflammation and in the growth of tumours, angiogenesis progresses from a physiological process to a pathological process.

This means that a drug like dextrin 2-sulphate or dextrin 6-sulphate or dextrin 2,6-sulphate which reduces and/or prevents the proliferation of endothelial cells and prevents neo-angiogenesis during the earliest stages of a pathological disease process could abort or even prevent the damage to the tissue which would occur as a consequence of the chronic inflammatory response. The aim of such a drug would be to prevent the slow progression to tissue destruction and fibrosis which is induced by the angiogenic response seen in chronic inflammation.

b) Tumour Growth and Metastasis

There has been considerable research into the role of angiogenesis in tumour growth. Early in the pathogenesis of a tumour, and before a tumour becomes clinically significant, there must be a switch to an angiogenic phenotype. This angiogenic switch can be mediated by either an increase in the expression of angiogenic factors, or by a decrease in the expression of angiostatic factors, or both. Many factors have been implicated in the control of tumour associated angiogenic activity including vascular endoihelial growth factor (VEGF), basic fibroblast growth factor (bFGF) and the CXC chemokines. We have already shown that dextrin 2-sulphate and dextrin 6-sulphate do not interfere with the proliferative action of vascular endothelial growth and basic fibroblast growth factor on primary endothelial cells or the KSY-1 cell line. The spread and growth of distal metastases can only be accomplished by individual cells which have been able to disseminate throughout the body and which can stimulate an angiogenic response.

Therefore, only when the metastatic deposit of cells has made the switch to an angiogenic phenotype will the rate of proliferation of these cells be sufficiently fast for the metastatic focus to become clinically evident. An effective inhibitor of endothelial cell mediated proliferation would therefore prevent further growth of the primary tumour and halt the development of metastases. Since tumour endotheliurn itself is not genetically abnormal, and therefore not subject to a high rate of mutation, it is most unlikely to develop drug resistance to angiostatic therapy.

This means that a drug like dextrin 2-sulphate or dextrin 6-sulphate or dextrin 2,6-sulphate which reduces or prevents the proliferation of endothelial cells and prevents neo-angiogenesis during the earliest stages of the growth of the metastasis could abort or even prevent the development of the metastatic lesion.

c) Diabetic Nephropathy and Retinopathy

Microvascular disease which manifests as new vessel formation is the most serious form of tissue damage which occurs in diabetic patients. Its most serious manifestation is microangiopathy which leads to diabetic nephropathy and to diabetic retinal eye disease. Microvascular changes are also thought to contribute to diabetic neuropathy and to diabetic foot disease. Although poor glucose control is a major contributing factor, it is not the sole factor responsible for this pathological disease process.

Both diabetic nephropathy and diabetic retinopathy have a multifactorial pathogenesis. There are changes in endothelial cells, thickening of the capillary basement membranes, decreased numbers of intramural pericytes, tissue hypoxia and increased retinal blood flow. In the case of the retina, changes in the arterioles, capillaries and veins lead to the formation of new blood vessels at the margins of the ischaemic area. This is thought to result in the release of angiogenic factors which promote new blood vessel formation. Angiogenic factors with properties similar to those isolated from some tumours have been isolated from the retinae of several species. This stimulus to neo-vascularisation results in a proliferative retinopathy whose features are the growth of new blood vessels. Haemorrhage from these fragile new vessels often leads to blindness.

Many patients with diabetic nephropathy develop chronic renal failure. They are often treated using continuous ambulatory peritoneal dialysis. This requires the use of dialysis solutions such as glucose or dextrin. By adding a sulphated dextrin at an appropriate concentration to the dextrin dialysis solution, it should be possible to reduce further damage to the kidney by inhibiting the angiogenic response which is driving it. Animal studies have shown that when sulphated dextrins are administered intraperitoneally, they accumulate in the kidney. By also monitoring the retinas of these patients, it will be possible to establish whether sulphated dextrins delivered intraperitoneally will prevent new blood vessel formation (ie: diabetic retinopathy) in the eye.

d) Rheumatoid Arthritis

Rheumatoid arthritis is a chronic inflammatory disease which is characterised by a progressive destruction of joints. The hallmarks of the pathological changes in the synovium include hyperplasia of synovial lining cells and follicle-like aggregation of lymphocytes and plasma cells. This inflammation of the synovium leads to the formation of a highly vascularised pannus and to the eventual destruction of the joint. The tissue destruction is partly dependent on proteases and collagenases which are released during the angiogenic response.

Although pathological studies have identified capillary damage, oedema, vascular congestion and a cellular infiltrate as early pathological changes in the rheumatoid synovium, the factors which initiate the disease process and lead to this chronic inflammation still remain unclear. Hirohata S & Sakakibara J, Lancet : Angiogenesis as a possible elusive triggering factor in rheumatoid arthritis. Apr. 17, 1999, page 1331, it was noted that neo-angiogenesis precedes all the other features of rheumatoid arthritis such as lining cell proliferation and cellular infiltration by one to two years. Although it has been shown that the cells lining the synovium produce angiogenic growth factors such as basic fibroblast growth factor and vascular endothelial growth factor in the synovium of early rheumatoid arthritis, in its earliest stages, the synovium show neo-angiogenesis without lining cell proliferation. This confirms that angiogenesis is the primary pathological event which is triggered by an unknown antigen. Therefore, intervention with a drug like dextrin 2-sulphate or dextrin 6-sulphate or dextrin 2,6-sulphate which reduces or prevents endothelial cell proliferation and neo-angiogenesis during its earliest stages could be beneficial for both the treatment of early rheumatoid arthritis and for preventing the destructive arthritis which eventually develops.

e) Inflammatory Bowel Disease

Crohn's Disease and Ulcerative Colitis are the major forms of inflammatory bowel disease. These chronic inflammatory disorders of the gastrointestinal tract are triggered by an unknown pathogen. Their pathology is characterised by a chronic leucocyte infiltrate in the bowel wall which leads to progressive tissue damage. The intestinal microvasculature has been implicated as playing a major role in the pathogenesis and the progression of inflammatory bowel disease. Immunohistochemical studies of tissue from patients with active inflammatory bowel disease have shown that the microvascular endothelial cells express high levels of E-selection, intercellular adhesion molecule-1 (ICAM-1) and CD31. These adhesion molecules mediate the binding and transmigration of circulating leucocytes. Thus altered endothelial cell function is associated with persistent chronic inflammation in both Crohn's Disease and in Ulcerative Colitis.

In the case of these two disorders, it is possible that the intraperitoneal administration of dextrin 2-sulphate or dextrin-6 sulphate or dextrin 2,6-sulphate would be of therapeutic benefit. Intraperitoneal administration of the drug results in substantial amounts of the drug accumulating in all of the tissues associated with the small bowel and the large bowel. This could result in a reduction in the number of activated, proliferating endothelial cells, as well as preventing the activation and proliferation of new populations of endothelial cells. This in turn would prevent neo-angiogenesis and the continuation of the chronic inflammatory response which leads to the development of clinical disease.

f) Psoriasis

This is a skin disorder which is characterised by an inflammatory cell infiltrate, abnormal proliferation of keratinocytes and dermal neo-vascularisation. Whilst it is recognised that the angiogenesis associated with psoriasis is not the primary cause of the pathogenesis of this disease, the angiogenic activity is nevertheless due to a combination of over production of IL-8 and an underproduction of the angiogenesis inhibitor, thrombospondin-1. There is also an over-expression of other angiogenic factors such as vascular endothelial growth factor and transforming growth factor-alpha. The angiostatic factor IP10 is expressed in psoriatic plaques with expression being reduced after successful treatment of the active lesions. This serves to highlight the importance of endogenous angiostatic factors in angiogenesis dependent disorders. Interestingly, many commonly used treatments for psoriasis such as topical steroids, cyclosporine and retinoids have angiostatic activity.

Therefore, the regular application of a topical (ie: skin) preparation of dextrin 2-sulphate or dextrin &sulphate or dextrin 2,6-sulphate to active plaque lesions of psoriasis could result in the healing of these lesions by reducing or preventing endothelial cell proliferation and the angiogenic response which is driving the development of the psoriatic lesion.

What is claimed:

1. A method of treating a patient having an angiogenesis-dependent disease or disorder, other than a highly vascular tumour, which comprises administering linear dextrin sulphate to the patient.

2. The method of claim 1 wherein said disease or disorder has chronic inflammation as a significant component of the process of the disease or disorder.

3. The method of claim 2 wherein said disorder is diabetic nephropathy or retinopathy, rheumatoid arthritis, inflammatory bowl disease or psoriasis.

4. The method of claim 1 wherein the dextrin sulphate is administered to the patient intraperitoneally.

5. The method of claim 1 wherein the dextrin sulphate is derived from a dextrin having at least 50% by weight of glucose polymers of DP greater than 12.

6. The method of claim 1 wherein the dextrin sulphate is derived from a dextrin containing less than 10% by weight of glucose polymers of DP less than 12.

7. The method of claim 1 wherein the dextrin sulphate is derived from a dextrin having a weight average molecular weight of from 10,000 to 35,000.

8. The method of claim 1 wherein the dextrin sulphate is derived from a dextrin containing less than 10% by weight of glucose polymers of molecular weight greater than 40,000.

9. The method of claim 1 wherein the dextrin contains at most two sulphate groups per glucose unit.

10. The method of claim 1 wherein the dextrin sulphate contains at between 0.5 and 1.5 sulphate groups per glucose unit.

11. The method of claim 1 wherein the dextrin sulphate selected from the group consisting of dextrin-2-sulphate, dextrin-6-sulphate, and mixtures thereof.

12. The method of claim 1 wherein the dextrin sulphate is derived from a dextrin having more than 90% by weight of glucose polymers of DP greater than 12.

13. The method of claim 1 wherein the dextrin sulphate is derived from a dextrin containing less than 5% by weight of glucose polymers of DP less than 12.

14. The method of claim 1 wherein the dextrin sulphate is derived from a dextrin having a weight average molecular weight of from 15,000 to 25,000.

15. The method of claim 1 wherein the dextrin sulphate is derived from a dextrin containing less than 5% by weight of glucose polymers of molecular weight greater than 40,000.

16. A method of treating a patient having an angiogenesis-dependent disease or disorder, other than a highly vascular tumour, which comprises administering a medicament comprising dextrin sulphate to a patient.

17. The method of claim 16, wherein the dextrin sulphate is derived from a dextrin having at least 50% by weight of glucose polymers of DP greater than 12.

18. The method of claim 16, wherein the dextrin sulphate is derived from a dextrin containing less than 10% by weight of glucose polymers of DP less than 12.

19. The method of claim 16 wherein the dextrin sulphate is derived from a dextrin having a weight average molecular weight of from 10,000 to 35,000.

20. The method of claim 16 wherein the dextrin sulphate is derived from a dextrin containing less than 10% by weight of glucose polymers of molecular weight greater than 40,000.

21. The method of claim 16 wherein the dextrin contains at most two sulphate groups per glucose unit.

22. The method of claim 16 wherein the dextrin sulphate contains between 0.5 and 1.5 sulphate groups per glucose unit.

23. The method of claim 16 wherein the dextrin sulphate selected from the group consisting of dextrin-2-sulphate, dextrin-6-sulphate, and mixtures thereof.

24. The method of claim 16 wherein the dextrin sulphate is derived from a dextrin having more than 90% by weight of glucose polymers of DP greater than 12.

25. The method of claim 16 wherein the dextrin sulphate is derived from a dextrin containing less than 5% by weight of glucose polymers of DP less than 12.

26. The method of claim 16 wherein the dextrin sulphate is derived from a dextrin having a weight average molecular weight of from 15,000 to 25,000.

27. The method of claim 15 wherein the dextrin sulphate is derived from a dextrin containing less than 5% by weight of glucose polymers of molecular weight greater than 40,000.

\* \* \* \* \*